United States Patent [19]
Green et al.

[11] Patent Number: 5,476,479
[45] Date of Patent: Dec. 19, 1995

[54] HANDLE FOR ENDOSCOPIC SURGICAL INSTRUMENTS AND JAW STRUCTURE

[75] Inventors: David T. Green, Westport; Ernest Aranyi, Easton; Ian J. Tovey, Milford, all of Conn.

[73] Assignee: United States Surgical Corporation, Norwalk, Conn.

[21] Appl. No.: 371,515

[22] Filed: Jan. 11, 1995

Related U.S. Application Data

[63] Continuation of Ser. No. 932,230, Aug. 19, 1992, abandoned, which is a continuation-in-part of Ser. No. 781,069, Oct. 18, 1991, abandoned, which is a continuation-in-part of Ser. No. 765,993, Sep. 26, 1991, abandoned.

[51] Int. Cl.$^6$ ................................................. A61B 17/50
[52] U.S. Cl. ........................ 606/205; 606/207; 606/210
[58] Field of Search ..................................... 606/205, 206, 606/207, 208, 210, 170, 151, 158, 209, 198; 128/751, 4

[56] References Cited

U.S. PATENT DOCUMENTS

| | | |
|---|---|---|
| D. 246,190 | 10/1977 | Hodge . |
| 459,818 | 9/1891 | Pearson et al. . |
| 825,121 | 7/1906 | Frentzen et al. . |
| 943,263 | 12/1909 | Moraweck . |
| 1,310,982 | 7/1919 | Davis . |
| 1,452,373 | 4/1923 | Gomez . |
| 1,513,367 | 10/1924 | Brix . |
| 1,606,497 | 11/1926 | Berger . |
| 1,659,112 | 2/1928 | Littlejohn . |
| 1,749,261 | 3/1930 | Reisler . |
| 1,816,952 | 8/1931 | Bergman . |
| 1,855,546 | 4/1932 | File . |
| 2,034,785 | 3/1936 | Wappler . |
| 2,070,670 | 2/1937 | Marshall . |
| 2,363,334 | 11/1944 | Jones . |
| 2,397,823 | 4/1946 | Walter . |

(List continued on next page.)

FOREIGN PATENT DOCUMENTS

| | | |
|---|---|---|
| 0065054 | 11/1982 | European Pat. Off. . |
| 0157888 | 10/1985 | European Pat. Off. . |
| 0176351 | 4/1986 | European Pat. Off. . |
| 0240722 | 10/1987 | European Pat. Off. . |
| 0380874 | 8/1990 | European Pat. Off. . |
| 0392548 | 10/1990 | European Pat. Off. . |
| 0392547 | 10/1990 | European Pat. Off. . |

(List continued on next page.)

OTHER PUBLICATIONS

European Search Report, Application No. EP 93 11 3273.
ELMED Operating Instruments catalog.
Karl Storz Endoscope Operating Instruments catalog.
Solos Endoscopy Brochure.
Sklar Products "Surgical Instruments", 1973, pp. 67 and 100.
EPO Search Report.
Padgett Instruments Bulletin.

*Primary Examiner*—Richard J. Apley
*Assistant Examiner*—Beverly M. Flanagan

[57] ABSTRACT

An endoscopic or laparoscopic surgical instrument having an internally disposed ratchet mechanism located within a barrel portion of a handle assembly. The instrument includes a handle assembly having a pivoting handle and a stationary handle, a barrel portion to which an elongated body assembly is secured, and a ratchet mechanism for releasably positioning a tool mechanism located at the distal end of the body assembly at various increments. The ratchet mechanism comprises a pawl member and a rack member which are disposed within the handle assembly. A rotational knob and locking member may also be provided to lock the body assembly at various orientations to the longitudinal axis. The tool assembly includes novel atraumatic jaw mechanisms incorporating flexural characteristics to better gauge the force being applied to the captured tissue. The novel jaw mechanisms further includes increased tissue gripping surface area and multiple tissue handling portions which allow users to use fewer instruments and reduce the time to perform procedures.

33 Claims, 27 Drawing Sheets

U.S. PATENT DOCUMENTS

| | | |
|---|---|---|
| 2,601,513 | 6/1952 | Gladstone . |
| 2,618,268 | 11/1952 | English . |
| 2,642,871 | 6/1953 | Thuerig . |
| 2,668,538 | 2/1954 | Baker . |
| 2,723,666 | 11/1955 | Greenberg . |
| 2,790,437 | 4/1957 | Moore . |
| 2,796,065 | 6/1957 | Kapp ................................... 606/207 |
| 2,898,915 | 8/1959 | Kammer . |
| 2,898,916 | 8/1959 | Kammer . |
| 3,101,715 | 8/1963 | Glassman . |
| 3,209,753 | 10/1965 | Hawkins et al. ....................... 606/207 |
| 3,404,677 | 10/1968 | Springer . |
| 3,426,757 | 2/1969 | Shannon et al. . |
| 3,446,211 | 5/1969 | Markham . |
| 3,470,872 | 10/1969 | Grieshaber . |
| 3,503,398 | 3/1970 | Fogarty et al. . |
| 3,506,012 | 4/1970 | Brown . |
| 3,515,139 | 6/1970 | Mallina ................................. 606/207 |
| 3,646,939 | 3/1972 | Sklar . |
| 3,746,002 | 7/1973 | Haller . |
| 3,807,406 | 4/1974 | Rafferty et al. . |
| 3,871,379 | 3/1975 | Clarke . |
| 3,921,641 | 11/1975 | Hulka . |
| 3,964,468 | 6/1976 | Schulz . |
| 3,989,033 | 11/1976 | Halpern et al. . |
| 4,005,714 | 2/1977 | Hiltebrandt . |
| 4,043,323 | 8/1977 | Komiya . |
| 4,049,002 | 9/1977 | Fletschka et al. . |
| 4,049,714 | 9/1977 | Kletschka et al. . |
| 4,054,143 | 10/1977 | Bauer . |
| 4,411,653 | 10/1983 | Razi . |
| 4,428,374 | 1/1984 | Auburn . |
| 4,572,185 | 2/1986 | Rich . |
| 4,574,804 | 3/1986 | Kurwa . |
| 4,611,595 | 9/1986 | Klieman et al. . |
| 4,614,187 | 9/1986 | Mulhollan et al. . |
| 4,643,190 | 2/1987 | Heimberger . |
| 4,655,219 | 4/1987 | Petruzzi . |
| 4,662,371 | 5/1987 | Whipple et al. . |
| 4,669,647 | 6/1987 | Storace . |
| 4,712,545 | 12/1987 | Honkanen . |
| 4,760,848 | 8/1988 | Hasson ................................. 606/206 |
| 4,792,330 | 12/1988 | Lazarus et al. . |
| 4,813,407 | 3/1989 | Vogen . |
| 4,815,460 | 3/1989 | Porat et al. . |
| 4,819,633 | 4/1989 | Bauer et al. . |
| 4,830,002 | 5/1989 | Semm . |
| 4,872,456 | 10/1989 | Hasson . |
| 4,896,661 | 1/1990 | Bogert et al. . |
| 4,898,157 | 2/1990 | Messroghli et al. . |
| 4,909,789 | 3/1990 | Taguchi et al. . |
| 4,919,152 | 4/1990 | Ger . |
| 4,935,027 | 6/1990 | Yoon . |
| 4,950,273 | 8/1990 | Briggs . |
| 5,009,661 | 4/1991 | Michelson . |
| 5,026,379 | 6/1991 | Yoon . |
| 5,047,046 | 9/1991 | Bodoia ................................. 606/205 |
| 5,047,049 | 9/1991 | Salai ................................... 606/205 |
| 5,052,402 | 10/1991 | Bencini et al. . |
| 5,133,724 | 7/1992 | Wilson, Jr. et al. . |
| 5,147,378 | 9/1992 | Markham . |
| 5,147,380 | 9/1992 | Hernandez et al. . |
| 5,171,256 | 12/1992 | Smith et al. . |
| 5,171,258 | 12/1992 | Bales et al. . |
| 5,176,699 | 1/1993 | Markham . |
| 5,199,419 | 4/1993 | Remiszewski et al. . |
| 5,245,987 | 9/1993 | Redmond et al. ..................... 128/20 |
| 5,258,004 | 11/1993 | Bales et al. . |

FOREIGN PATENT DOCUMENTS

| | | |
|---|---|---|
| 0484671 | 5/1992 | European Pat. Off. . |
| 0543107 | 5/1993 | European Pat. Off. . |
| 543107A2 | 5/1993 | European Pat. Off. . |
| 2542188 | 9/1984 | France . |
| 840884 | 6/1952 | Germany . |
| 1065565 | 9/1959 | Germany . |
| 220437 | 4/1961 | Germany . |
| 1566060 | 6/1970 | Germany . |
| 2327921 | 12/1974 | Germany . |
| 3013836 | 10/1981 | Germany . |
| 9106506 | 5/1991 | Germany . |
| 9109097 | 10/1991 | Germany . |
| 0121537 | 6/1958 | U.S.S.R. ............................... 606/207 |
| 0004688 | of 1894 | United Kingdom ................... 606/207 |
| 2044108 | 10/1980 | United Kingdom . |
| 2086792 | 5/1982 | United Kingdom . |

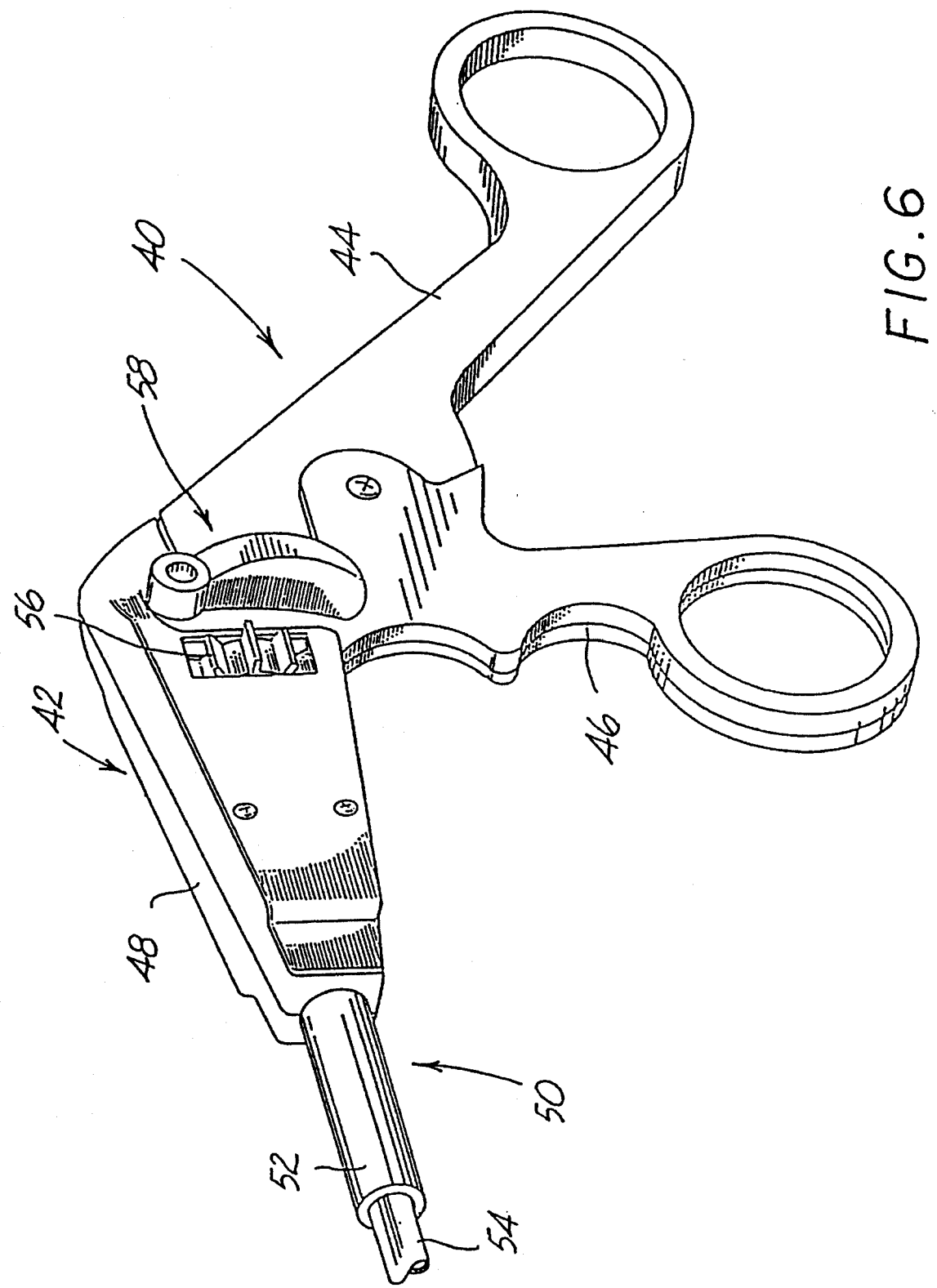

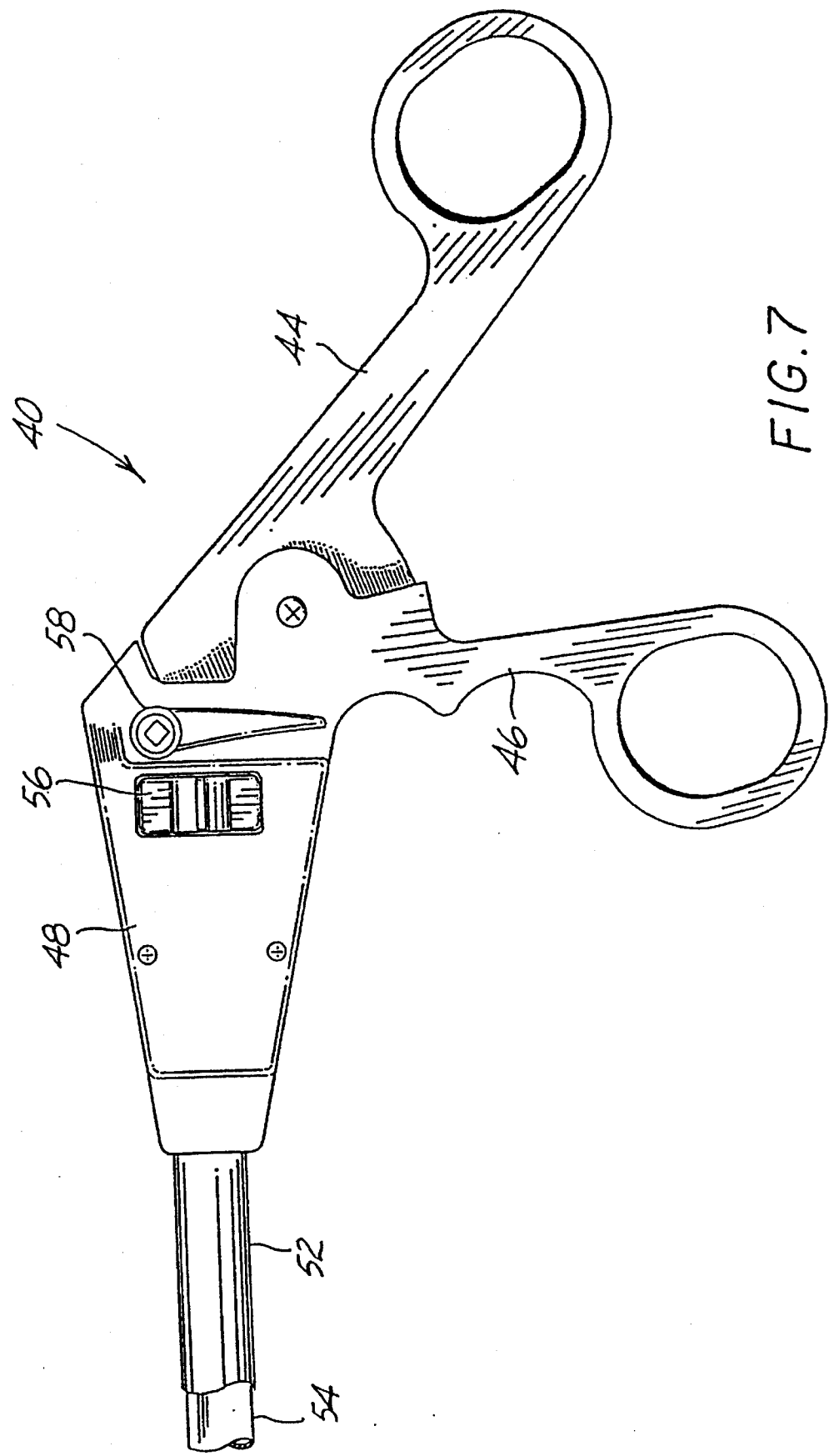

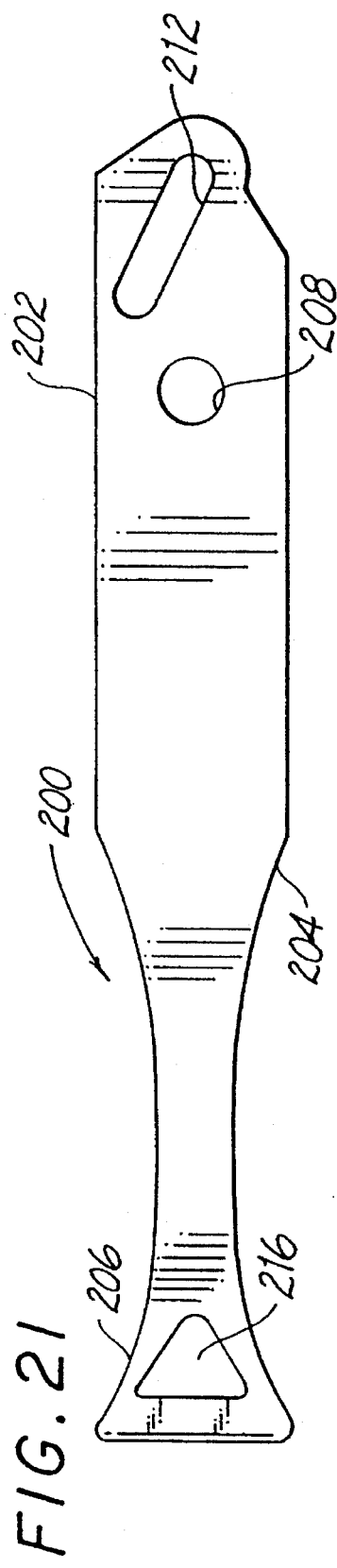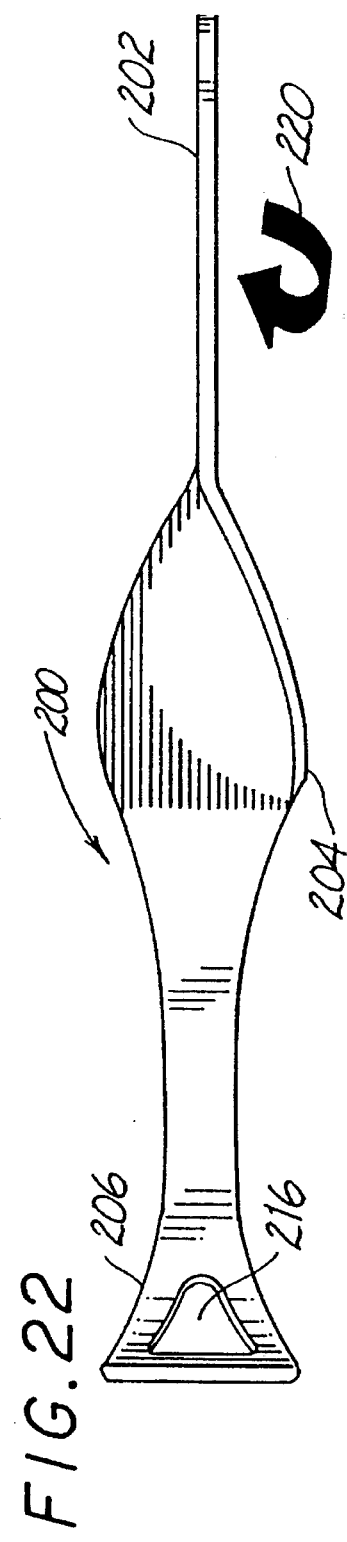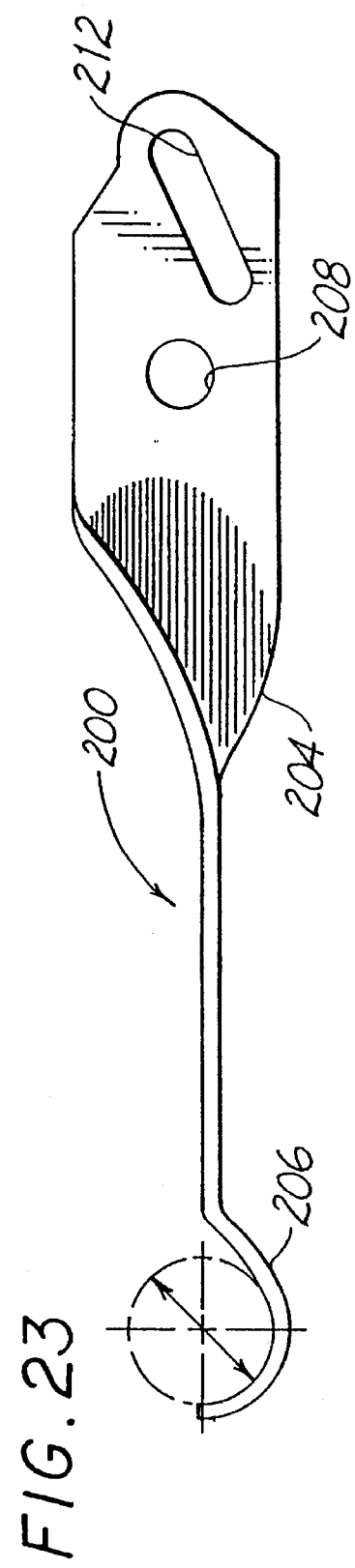

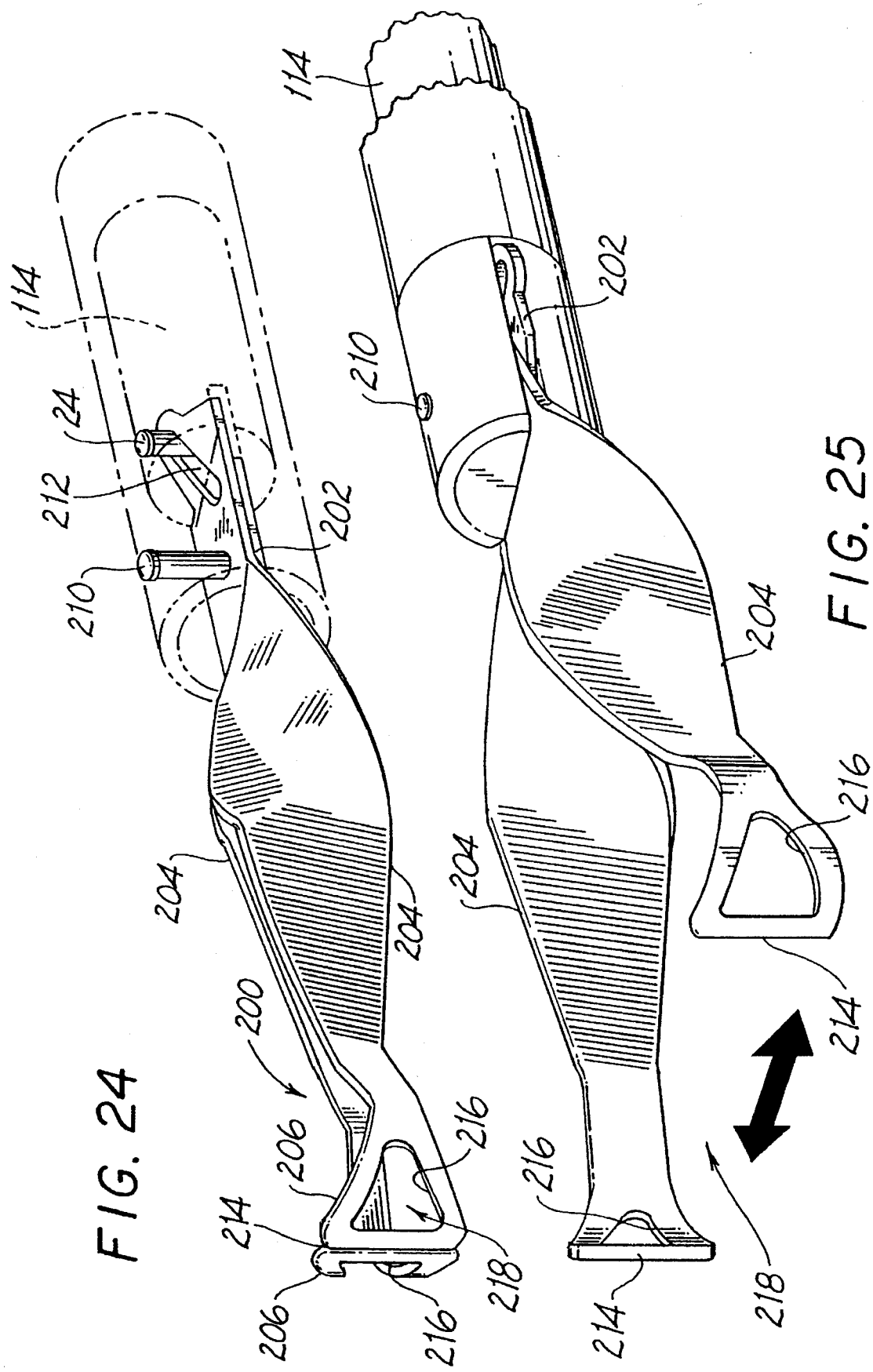

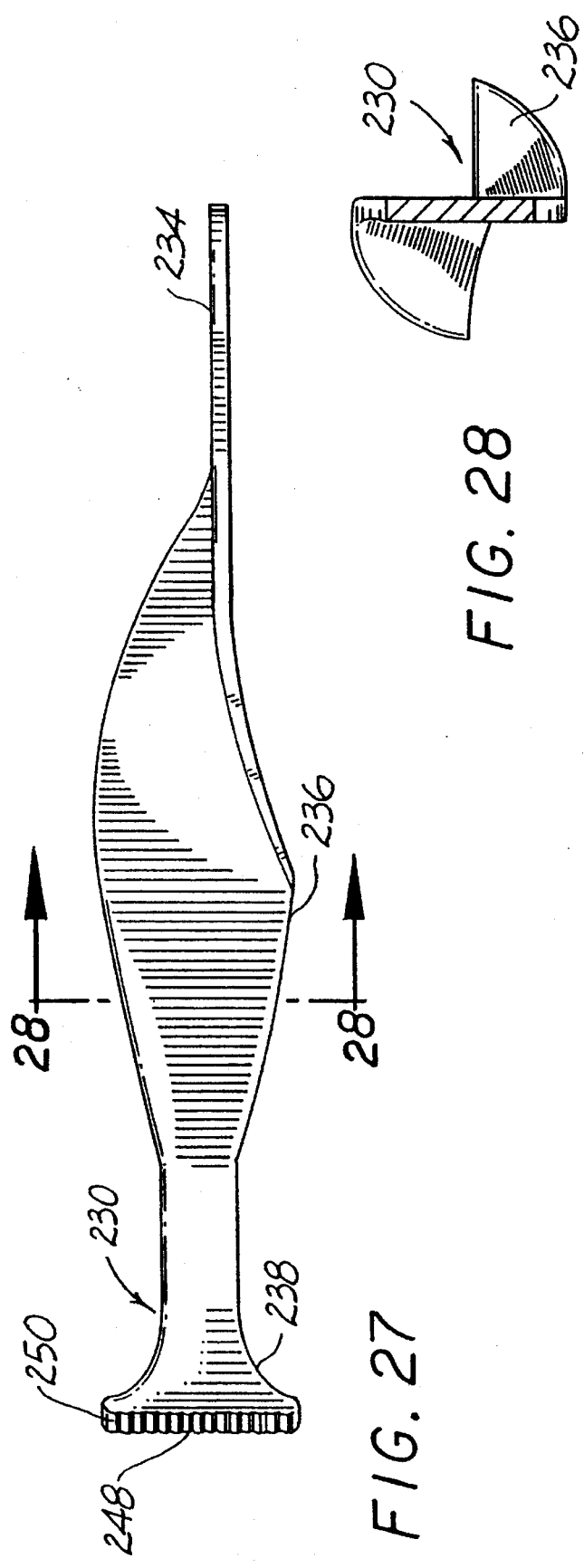
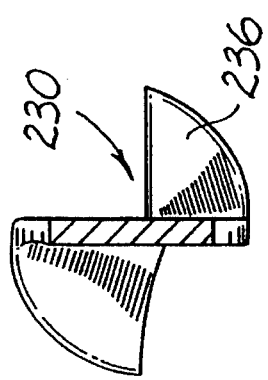
FIG. 28
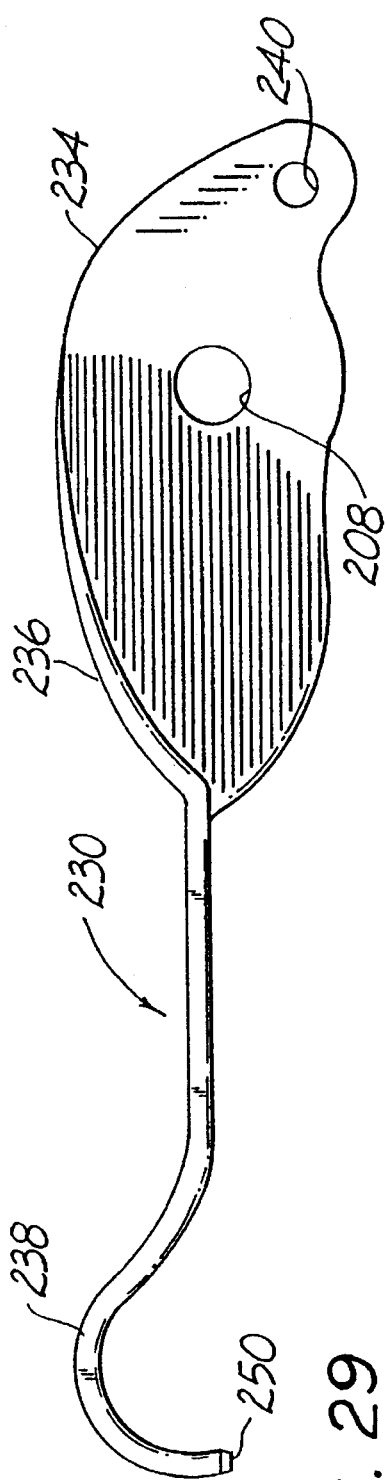
FIG. 27
FIG. 29

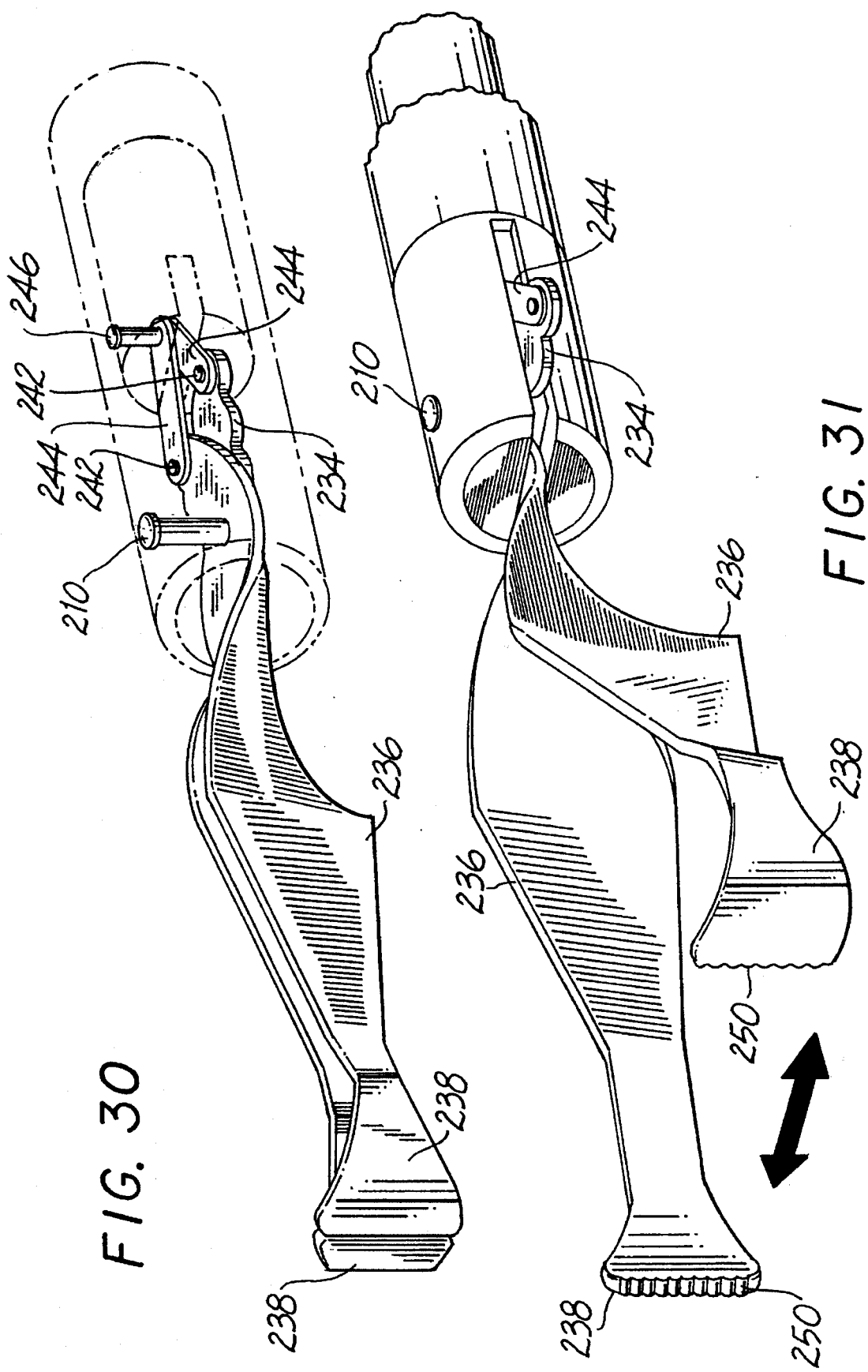

HANDLE FOR ENDOSCOPIC SURGICAL INSTRUMENTS AND JAW STRUCTURE

CROSS REFERENCE TO RELATED APPLICATION

This is a continuation of application Ser. No. 07/932,230 filed on Aug. 19, 1992 which is a continuation-in-part of application Ser. No. 07/781,069 filed on Oct. 18, 1991 which is a continuation-in-part of application Ser. No. 07/765,993 filed on Sep. 26, 1991; all applications now abandoned.

BACKGROUND OF THE INVENTION

1. Field of the Invention

The present invention relates to surgical instruments, and more particularly relates to handle and jaw structure for an endoscopic or laparoscopic surgical instrument having reciprocating jaw members which pivot in response to the opening and closing of the handle members, where movement of the handle members is translated through an elongated tubular body member to open and close the jaw mechanism. The present invention further relates to a ratchet mechanism which is internally disposed within the handle to provide incremental positioning of the jaw members in relation to each other. The present invention further relates to novel jaw members.

2. Discussion of the Prior Art

In the prior art, various endoscopic surgical instruments are disclosed which utilize generally complex mechanisms for opening and closing handle members and jaw members to facilitate use of the device at a surgical site. Many devices provide an intricate construction in which a linkage mechanism for opening and closing the jaws requires numerous moving parts, while a sliding arrangement is provided between two extended rod members to activate the linkage mechanism in response to movement of the handle members. In addition, pivoting of the handle members in many cases causes an unwanted radial torquing force on the rod which requires additional space to be provided in the handle members to accommodate the radial movement of the rod.

Furthermore, it is often necessary for the surgeon, or an assistant, to maintain a constant force on the handles to keep the jaw mechanism closed in the event that the instrument is a grasping or gripping device such as forceps, needle holders, or retractors. This limits the surgeon's range, and in the case of an assistant, requires additional personnel to be present in the operating room, thus restricting movement in an already confining location. To alleviate this problem, it has been known to provide locking mechanisms on the handles of the surgical instruments which allow the surgeon to lock or clamp the jaw members in place to free his hands to operate additional instruments during the course of the operation. This frees the surgical assistant to support the surgeon and eliminates the need for additional assistants. Typical locking devices include arm members which extend between the handles so that a series of ridges or ribs on each arm member engage corresponding ridges on the opposite arm to lock the handles in position. Bending one arm in relation to the other releases the locking mechanism.

A disadvantage associated with these devices concerns the release of the locking mechanism for subsequent movement of the jaw members to remove or reposition the instrument. Generally, the arm members of locking mechanisms are constructed of a resilient material, such as stainless steel or rigid plastic, and the locking forces which hold the arm members in engagement are generated by the natural flexing and biasing of the material of which the arm members are constructed. To release the locking mechanism, the arms must be disengaged by overcoming the locking forces of the arms. Typically, this is accomplished by manually flexing the arms away from each other, necessitating the use of two hands, one to grasp the instrument, and the other to forcibly move the arm members. This, of course, requires the surgeon (or assistant) to cease what he is doing and release the mechanism, thus reducing the effectiveness of the surgeon during the operation, particularly in an emergency situation.

A further disadvantage lies in the fact that typical locking mechanisms cannot be overridden; that is, the mechanism is always engaged, thereby preventing free movement of the handle and jaw mechanism. This usually requires the surgeon to choose an instrument either having the locking mechanism or one that does not. This leads to an overabundance of instruments in the operating room and tends to further complicate an already complex situation.

Finally, locking mechanisms located on the handles require special care in sterilization, packaging and storage, as well as in normal handling in the operating room. Dirt and debris may clog the ribs of the locking mechanism thus reducing its effectiveness, and damage to the ribs during storage or packaging may destroy the ribs, rendering the locking mechanism useless.

U.S. Pat. No. 1,452,373 to Gomez discloses a typical locking mechanism for a surgical instrument, in which a plurality of ribs are provided on an extension of the handle member which engage a similar rib member on the opposite handle. Once engaged, the handles must be moved away from each other perpendicular to their longitudinal axis to disengage the locking mechanism to release the jaw mechanism.

U.S. Pat. No. 4,896,661 to Bogert et at. disclose a surgical instrument having a ratchet mechanism positioned on the handle members which includes a curved rack member attached to one handle member which passes through a slot in the other handle member. A releasable pawl member is provided on the second handle to engage the rack member and provide a means for releasing the ratchet.

U.S. Pat. No. 4,935,027 to Yoon discloses a surgical instrument having a ratchet mechanism positioned between the handle members. A rack member is provided which extends from one handle and passes through a slot in the second handle to lock the handles in place. Pivoting the rack member away from corresponding grooves in the slot will release the ratchet mechanism.

U.S. Pat. No. 4,428,374 to Auburn discloses a surgical instrument having means for positioning and holding the handle members in relation to each other. A rack member is provided on one handle member which extends through a slot in the second handle member in which a releasable pawl mechanism is provided to engage and disengage the ratcheting mechanism.

With respect to jaw mechanisms and, in particular, atraumatic jaw mechanisms such as graspers and clamps, it is important for surgeons to be able to gauge or "feel" the amount of force being applied to the jaw mechanisms. This ability is particularly important in endoscopic procedures where visibility is somewhat limited and surgeons must place a greater reliance on their sense of touch. In conventional jaw mechanisms, the elements of the jaws are typically forged or cast of a rigid material into a predetermined shape. These forged or cast elements require elaborate metal working facilities and a relatively large amount of labor in finishing the elements. The finished elements usually exhibit very little flexural ability thus inhibiting the surgeon's perception of the amount of force to which the grasped or clamped tissue is exposed.

Additionally, manipulation of typical surgical instruments having jaw mechanisms creates risks to the surrounding tissue, particularly the tissue coming in contact with the distal end of the instrument where opposing jaw members meet. These risks are compounded in the endoscopic and laparoscopic environment where maneuverability of instruments as well as visibility in the entire surgical site are limited.

Furthermore, with respect to jaw members and, in particular, jaw members used for endoscopic or laparoscopic procedures where a limited number of access points to the surgical area through trocar cannulas is desired, it is necessary to keep instrumentation to a minimum. Previous devices function very well for their specific purposes, however, in conventional jaw mechanisms the gripping surface area is limited and separate instruments are required having different jaw structures for performing different functions, for example, forceps for gripping and pulling away tissue and graspers for atraumatically holding tubular vessels. Having to provide these separate instruments increases the time to perform the necessary procedures by requiring exchanging instruments in the cannulas or by creating additional access points using additional trocars.

The novel surgical instrument pursuant to the present invention obviates the disadvantages encountered in the prior art and provides a precise instrument which is easy to manufacture and efficient to use, which eliminates many of the moving parts required by prior art devices. The instrument of the present invention incorporates many features which are of use to the surgeon during an operation, including an internal ratcheting mechanism to provide for incremental movement of the tool mechanism and locking of the jaws if desired, while maintaining a lightweight construction in an easy to handle device in which all of the features may be operated with one hand. Also, the features are so positioned so as to provide a maximum line of sight for the surgeon without obstructing the view to the surgical site. Novel jaw mechanisms may also be incorporated which are easy to precisely manufacture and, in the case of atraumatic graspers or clamps, have flexural capabilities which allow surgeons to gauge the amount of force being applied. Furthermore, the jaw mechanisms may have novel multiple tissue handling portions which add gripping surface while keeping risks to surrounding tissue low and allow surgeons to use fewer instruments, therefore, reducing the time required to perform procedures.

SUMMARY OF THE INVENTION

The present invention provides a novel endoscopic or laparoscopic surgical device which incorporates many features necessary for endoscopic or laparoscopic surgical procedures, and provides a lightweight and easy to use device which may be operated with one hand. The device includes an internal ratcheting mechanism located preferably within the barrel of the handle mechanism which provides for incremental positioning of the tool mechanism for performing the surgical procedure. The device is simple to manufacture, and may incorporate any one of a series of jaw mechanisms for various surgical procedures. The device is a high precision instrument in which many moving parts normally associated with such a device are eliminated, thus reducing instances of mechanical failure requiring expensive repair or ultimate destruction of the instrument.

The endoscopic or laparoscopic surgical instrument of the present invention comprises a handle assembly, an elongated body assembly and a tool mechanism. A ratchet mechanism may be attached within the barrel portion of the handle assembly. The handle assembly includes a stationary handle and pivoting handle, attached to the barrel portion, and the body assembly is attached to the barrel portion and extends therefrom. The body assembly consists of an outer tubular member and an inner rod member which coaxially passes within the outer tubular member. The rod member is attached to the pivoting handle, while the tube member is secured in a conventional manner to the barrel portion which extends into the stationary handle. As the pivoting handle moves, the rod member slidably reciprocates within the outer tube member.

Attached to a distal end of the body assembly is the tool mechanism which opens and closes in response to movement of the pivoting handle in relation to the stationary handle. The tool mechanism may comprise a jaw mechanism with a pair of jaw members wherein one or both jaw members open and close to perform various endoscopic or laparoscopic surgical procedures. The tool mechanism includes, but is not limited to, a scissor device, a dissecting device, a grasping device, a retractor device, and like mechanisms.

The present invention further includes novel atraumatic jaw mechanisms having flexural characteristics which serve to better transmit to the user a more accurate gauge of the force being applied to the captured tissue. This is accomplished by fabricating the jaw members of a material or in a configuration which permits the jaw members to flex and allow the user to gauge the amount of force applied to the tissue by the jaw mechanism. This flexural ability reduces the likelihood of unintentional traumatic injury, particularly in reduced visibility, endoscopic or laparoscopic procedures. In particularly advantageous embodiments, the jaw members are fabricated using a unique manufacturing technique which eliminates the need for elaborate and expensive metal working equipment. This technique includes fabricating the individual jaw members from a single sheet of malleable material and twisting or bending the jaw members into a predetermined position.

The novel atraumatic jaw of the present invention also includes a tissue gripping face which affords the surgeon greater flexibility with a single instrument by providing additional gripping surface and the ability to perform different functions, e.g., grasping a tubular vessel atraumatically or gripping tissue so as to separate tissue or organs from each other. The tissue gripping face further includes the feature of a plurality of teeth disposed along the surface thereof. An end portion of the tissue gripping portion is rounded and is preferably protruding distally away from the tissue gripping face as well as from the opposing jaw member. This feature reduces the risk to surrounding tissue by preventing tissue which is not intended to be grasped from entering between the opposing jaw members at the distal end. The teeth may also be provided with a truncated semicircular shape so that when the jaw members are disposed opposite each other in a particular fashion the teeth abut one another to grip tissue therebetween. The truncated semicircular shape provides an atraumatic abutment surface for the gripping of tissue. Alternatively, the opposing jaw members may be configured so that the corresponding opposing teeth mesh.

The present invention also includes the provision of a second pivot point on the pivoting handle, to which the inner rod member is attached. As the handle pivots, the second pivot point rotates to allow the inner rod to move longitudinally in the outer tube with minimal radial deflection. This feature reduces the radial wear on the inner rod and prevents weakening of the structure during long term use. In addition, it allows for a reduction of the required internal spacing between the outer tube and inner rod to result in a more compact and streamlined instrument. Furthermore, unwanted torquing forces are eliminated at the pivot point thus minimizing the possibility of mechanical breakdown of the instrument at the connection between the pivoting handle and the movable inner rod.

The present invention may include the provision of a rotatable knob on the outer tubular member to allow the body assembly and tool mechanism to rotate to position the jaws at desired angles to the longitudinal axis during the surgical procedure. Preferably, the rotatable knob is secured to the outer tube and positioned in a slot which passes through the barrel portion of the stationary handle, so that a surgeon may rotate the knob, and consequently the body assembly and jaw mechanism, through the use of his thumb while he is holding the stationary handle with his fingers. This frees the surgeon's other hand to simultaneously operate another instrument during surgery.

Another novel feature of the present invention is the provision of a ratchet mechanism located internally within the barrel of the handle assembly to provide for incremental movement of the jaw mechanism. Since it is located internally within the barrel portion of the handle assembly, it is not subjected to environmental conditions which may result in clogging or damage to the ratchet mechanism during handling and storage. Furthermore, the novel ratchet mechanism of the present invention provides for simple handling and maneuvering during the surgical procedure and allows the surgeon to operate the device with one hand, thus freeing his other hand for performing other functions during the surgical procedure.

The ratchet mechanism of the present invention includes a trigger mechanism for engaging and disengaging the ratchet feature. In a first embodiment, a rack member is provided on the surface of the pivoting handle which engages the pawl arm of the trigger portion of the ratchet mechanism. The pawl arm is biased by a leaf spring member which maintains the pawl arm in contact with the rack member. The trigger member, when depressed, overcomes the force of the leaf spring and pivots the pawl arm away from the rack member to release the ratchet mechanism. If the trigger mechanism is continually pressed, the ratchet mechanism is overridden and the device functions as a conventional surgical instrument. The trigger mechanism is preferably positioned on the barrel portion of the stationary handle member. The rack member consists of a plurality of indentations or notches into which the pawl arm fits to secure the handles in incremental positions during operation of the tool mechanism.

A second embodiment of the ratchet mechanism of the present invention provides the trigger mechanism positioned on the stationary handle at the barrel portion and includes a pawl arm which engages a rack member which is constructed integral with the inner rod member of the body assembly. The rack member may comprise a plurality of indentations cut into the rod member which engage the pawl arm of the trigger mechanism. The trigger mechanism is spring biased so that the pawl arm is continually engaged with the rack member. Constant depression of the trigger mechanism overrides the ratchet mechanism and the handles may be operated as in a conventional tool.

Alternatively, the indentations may be part of a block device which is secured to the rod member and provided with the plurality of indentations or notches to engage the pawl arm. Preferably, however, the notches or indentations are constructed integral with the rod member, and in a preferred embodiment are provided as a series of circumferential notches about the rod member. This allows for the provision of a rotatable body assembly through the use of a rotation knob which provides 360°, or any portion thereof, rotation of the body assembly to rotate the jaws of the tool mechanism to desired angles along the longitudinal axis of the instrument during the surgical procedure. Accordingly, the ratchet mechanism may operate at any orientation of the jaw members.

In order to provide a complete override feature of the ratchet mechanism, the present invention may include a novel actuator device which cooperates with the trigger mechanism to provide an on/off mechanism for the ratchet feature. In this embodiment, the trigger mechanism includes an articulated body portion having a projection or finger-like member which acts as a camming member to engage the actuator means. The actuator means essentially comprises a pivotable camming member having a slot into which the finger-like projection extends. When pivoted in a first direction, the camming slot engages the camming member of the articulated body and causes the body to pivot into engagement with the circumferential rack disposed on the inner rod member. When the actuator means is pivoted in a second direction, the camming slot is of such a configuration so as to disengage with the camming member of the articulated body which causes the pawl arm to fall out of engagement with the rack means of the inner rod member. In this embodiment, the trigger mechanism is also spring biased so that when the actuator means is in the "on" position, the pawl arm is biased into engagement with the rack means.

A further optional feature of the present invention is the provision of a stop mechanism to arrest rotation of the body assembly. The stop mechanism is provided in conjunction with the rotation knob and allows the surgeon to lock the body assembly at a particular orientation during rotation. The lock mechanism is provided on the barrel portion of the handle assembly and is positioned so that the surgeon may activate the lock mechanism with a single hand.

The present invention may also feature a connection port to provide the device with electrocautery capabilities. A connection port allows for the connection of a suitable jack member to be inserted into the device. The outer tube of the body assembly is provided with electrical insulation, preferably heat shrink tubing, which extends a substantial portion of the length of the outer tube. In this embodiment, the handle is molded of plastic material to provide electrical insulation for the user.

In the preferred embodiment, all the above features are incorporated into a single endoscopic and laparoscopic surgical instrument, so that the instrument has electrocautery, rotational, and ratcheting capabilities. However, the instrument of the present invention is constructed with at least the ratcheting capabilities to provide for incremental adjustment of the tool mechanism during a surgical procedure.

Accordingly, it is an object of the present invention to provide an endoscopic or laparoscopic surgical instrument in which all the features may be used by a surgeon with one hand.

It is another object of the present invention to provide an endoscopic or laparoscopic surgical instrument having ratcheting capabilities in which the ratchet mechanism is located internal of the handle assembly of the device.

It is a further object of the present invention to provide an endoscopic or laparoscopic surgical instrument in which the ratcheting mechanism may be overridden to allow for full movement of the handles of the device.

It is still a further object of the present invention to provide an endoscopic or laparoscopic surgical instrument in which a ratchet mechanism is provided along with a rotational body assembly so that the ratchet mechanism may be operated at any orientation of the tool mechanism.

It is another object of the present invention to provide novel jaw mechanisms which enable users to gauge the degree of force applied to the jaw members or to tissue captured therebetween.

It is another object of the present invention to provide a method of fabricating jaw mechanisms without the need for elaborate metal working facilities.

It is a further object of the present invention to provide novel atraumatic jaw mechanisms which have additional gripping surface and enable users to perform different tissue handling functions with a single instrument.

BRIEF DESCRIPTION OF THE DRAWINGS

The foregoing objects and other features of the invention will become more readily apparent and may be understood by referring to the following detailed description of an illustrative embodiment of the endoscopic or laparoscopic surgical instrument having an internal ratchet mechanism, taken in conjunction with the accompanying drawings, in which:

FIG. 6 illustrates a perspective view of an alternate embodiment of the endoscopic or laparoscopic surgical instrument employing the ratchet mechanism of the present invention;

FIG. 7 illustrates a side plan view of the laparoscopic surgical instrument of FIG. 6;

FIG. 21 illustrates a top plan view of a jaw member in accordance with one embodiment of the present invention prior to being formed;

FIG. 22 illustrates a top plan view of the jaw member of FIG. 21 wherein a proximal end is bent relative to the distal end;

FIG. 23 illustrates a side plan view of the jaw member of FIG. 22 wherein the distal end is formed in a semicircular configuration;

FIG. 24 illustrates a perspective view in partial phantom of a jaw mechanism in accordance with one embodiment of the present invention with the jaw members closed;

FIG. 25 illustrates a perspective view of the jaw mechanism of FIG. 24 with the jaw members in the open position;

FIG. 27 illustrates a top plan view of a jaw member in accordance with another embodiment of the present invention;

FIG. 28 illustrates a front plan view in cross section of a jaw member taken along line 28–28 of FIG. 27;

FIG. 29 illustrates a side plan view of the jaw member of FIG. 27;

FIG. 30 illustrates a perspective view in partial phantom of a jaw mechanism in accordance with jaw members of FIG. 27 in the closed position;

FIG. 31 illustrates a perspective view of the jaw mechanism of FIG. 30 with the jaw members in the open position;

DETAILED DESCRIPTION OF THE PREFERRED EMBODIMENTS

Figure 1:
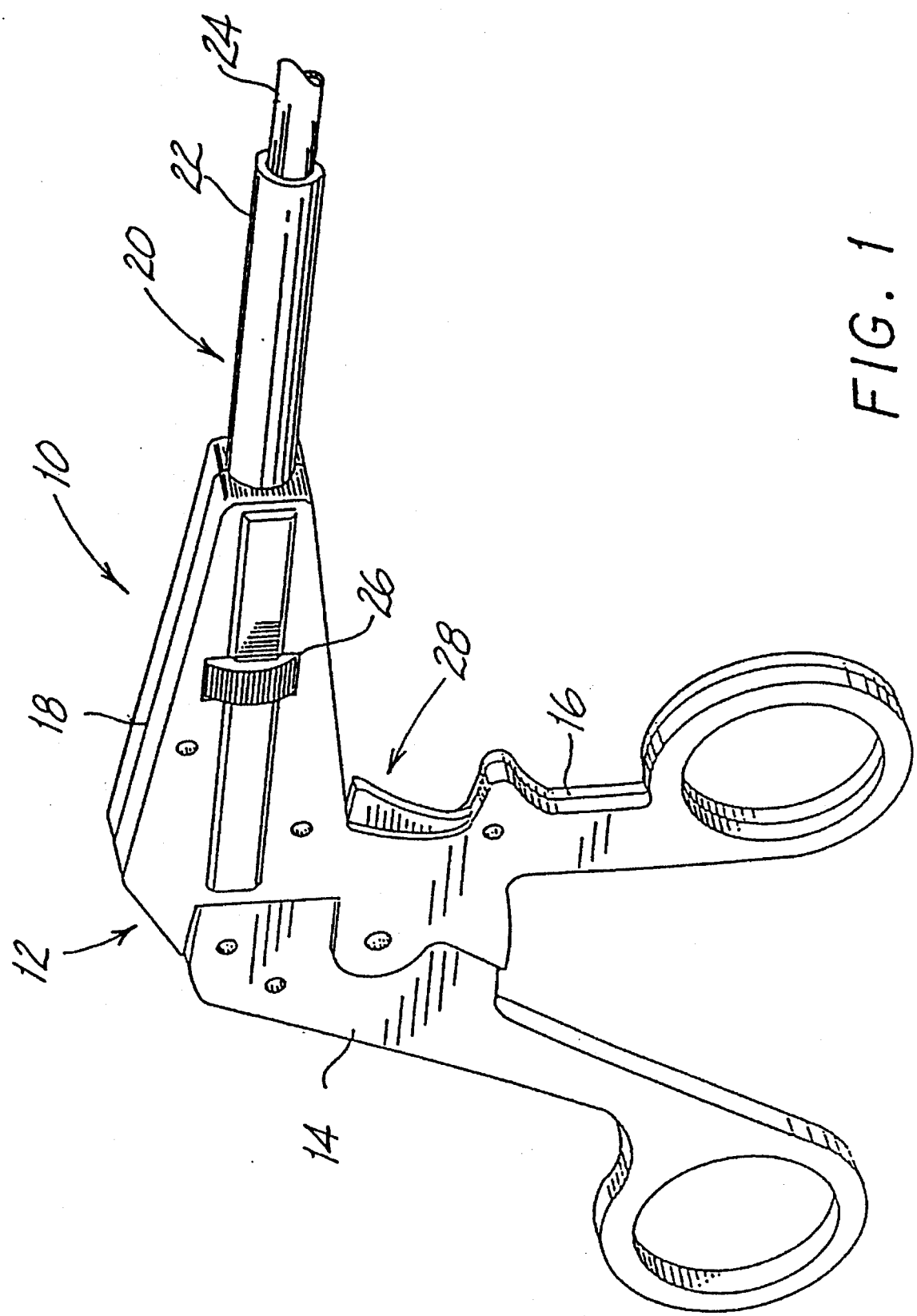
FIG. 1 illustrates a perspective view of an endoscopic or laparoscopic surgical instrument possessing the ratchet mechanism according to a first embodiment of the present invention.

Referring now in specific detail to the drawings, in which like reference numerals identify similar or identical elements, FIG. 1 illustrates a first embodiment of the endoscopic or laparoscopic surgical instrument 10. In its simplest form, device 10 comprises a handle assembly 12, a body assembly 20, and a ratchet mechanism 28. Handle assembly 12 comprises a pivoting handle 14, a stationary handle 16, and a barrel portion 18 to which body assembly 20 is attached. Body assembly 20 essentially comprises an outer tubular member 22 through which an inner rod member 24 coaxially passes in a slidable arrangement. Preferably, outer tube 22 is secured to barrel portion 18 and remains stationary during operation of the device. Upon movement of pivoting handle 14, inner rod 24 reciprocates within tube member 22 to operate a tool mechanism provided at the distal end of the instrument 10. This tool mechanism (not shown) may comprise a surgical implement, such as scissors, graspers, forceps, retractors and the like. A rotation knob 26 may be provided which rotates body assembly 20 to orient the tool mechanism at various angles to the longitudinal axis.

Figure 2:
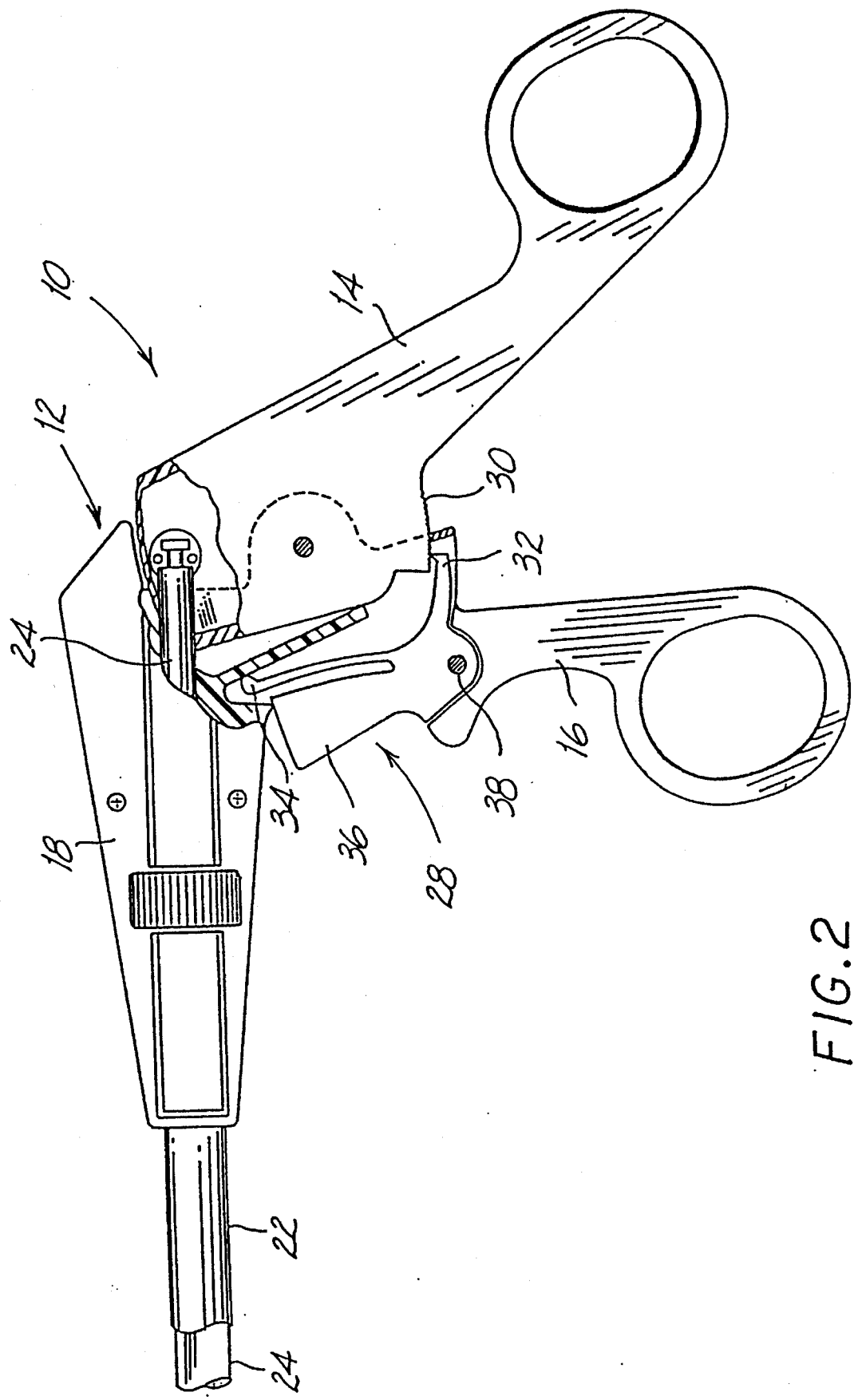
FIG. 2 illustrates a side plan view and partial cut-away of the surgical instrument of FIG. 1.
Figure 3:
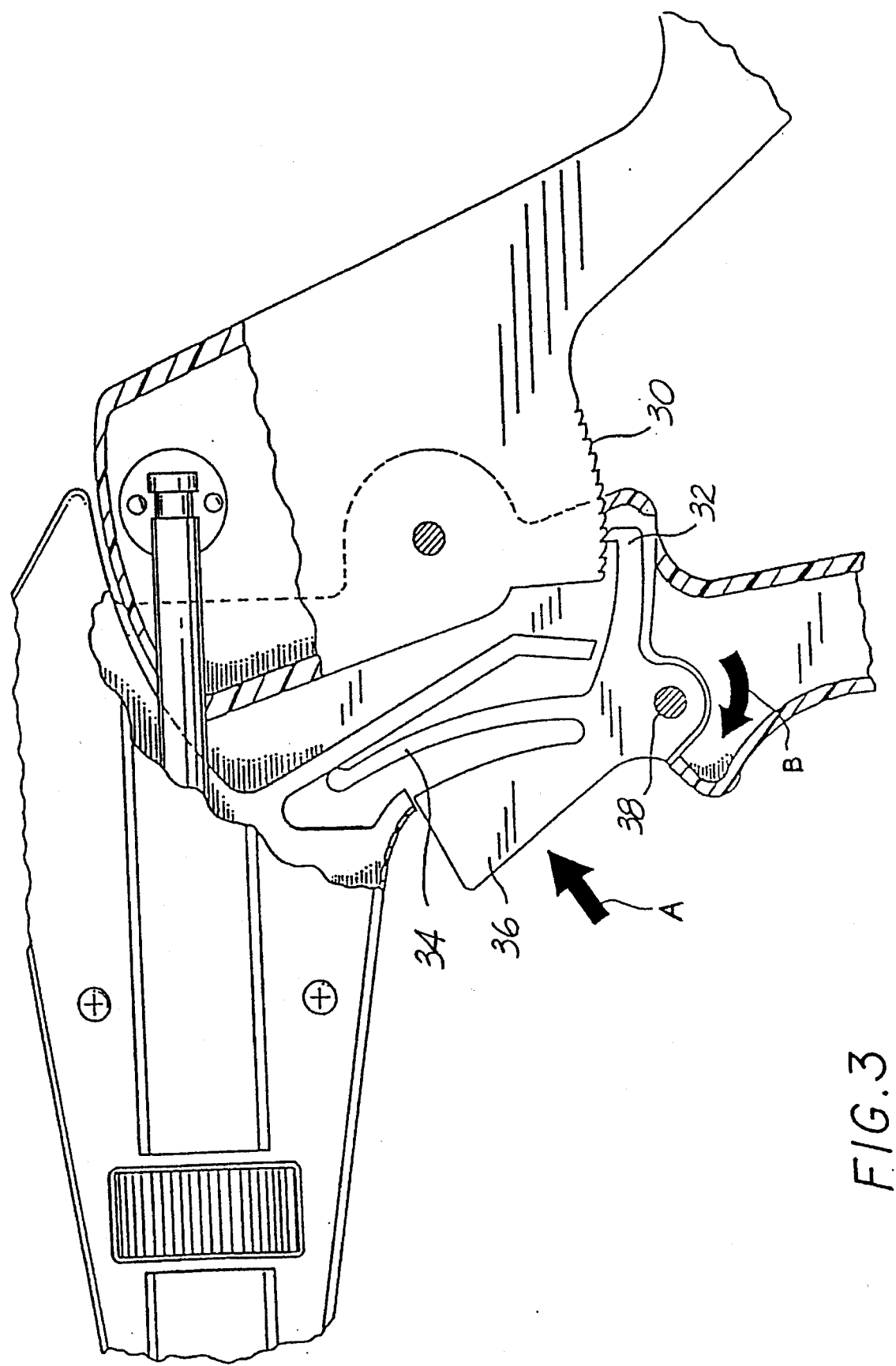
FIG. 3 illustrates an exploded side cut-away view of the device of FIG. 2 showing in detail type ratchet mechanism according to the present invention.

As best seen in FIGS. 2 and 3, ratchet mechanism 28 is provided to incrementally adjust and hold the position of pivoting handle 14. This incremental positioning, which sets pivoting handle 14 at various locations along its path of travel, provides a means to incrementally open and close the tool mechanism during the surgical procedure. Ratchet mechanism 28 is essentially positioned internally within barrel portion 18 and stationary handle 16 so that none of the mechanism is exposed to environmental conditions.

Figure 5:
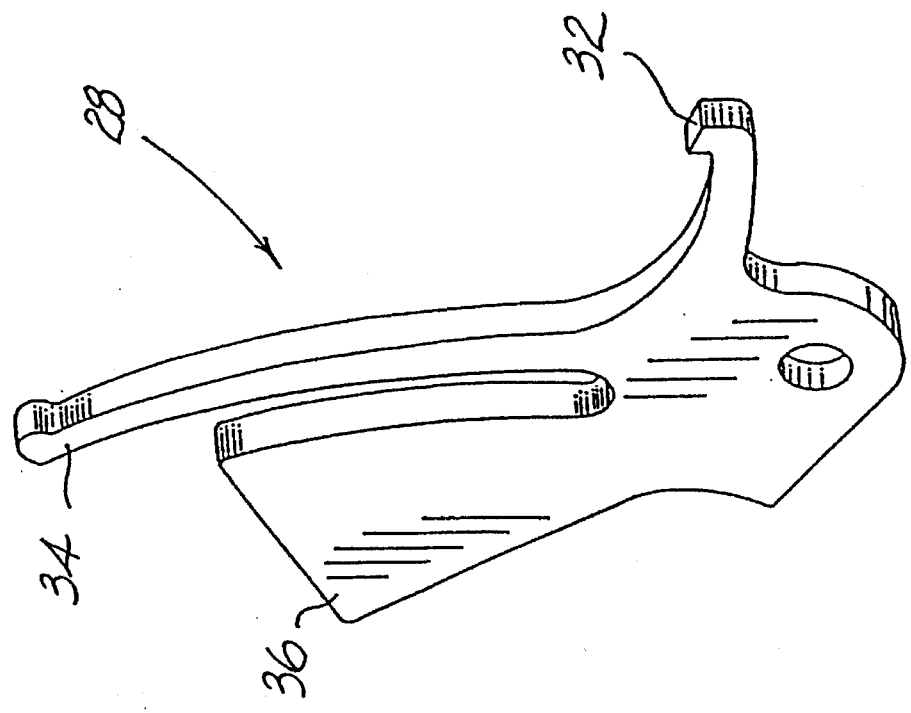
FIGS. 4 and 5 illustrate a side plan view and a perspective view, respectively, of the ratchet mechanism of the embodiment of FIG. 1.
Figure 4:
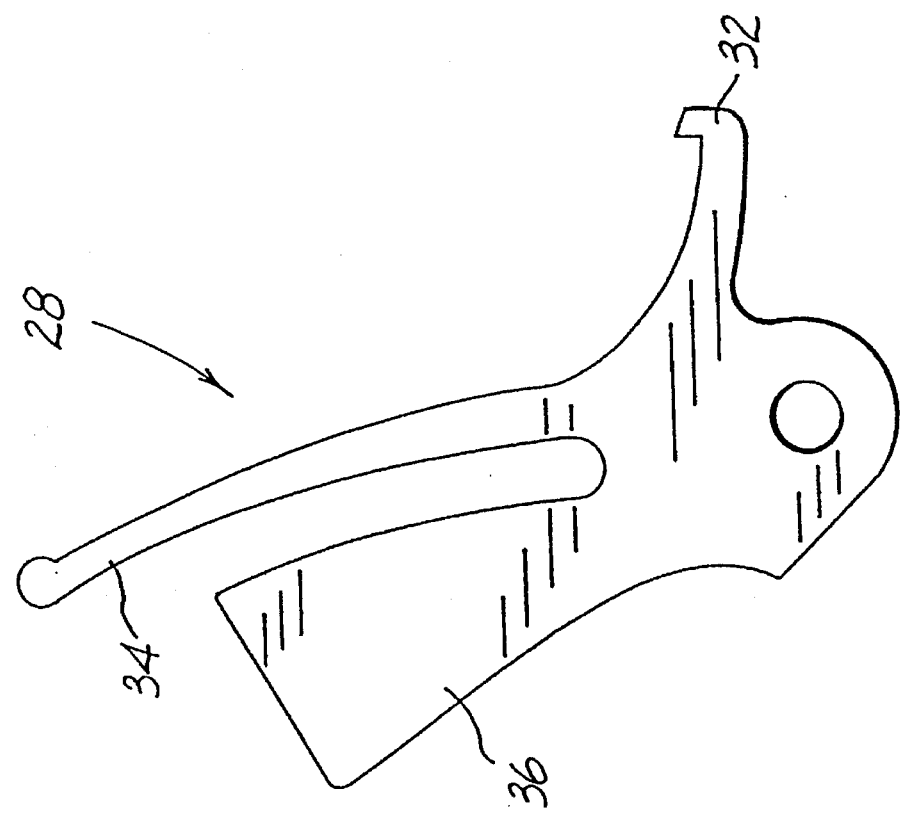
Figure 8:
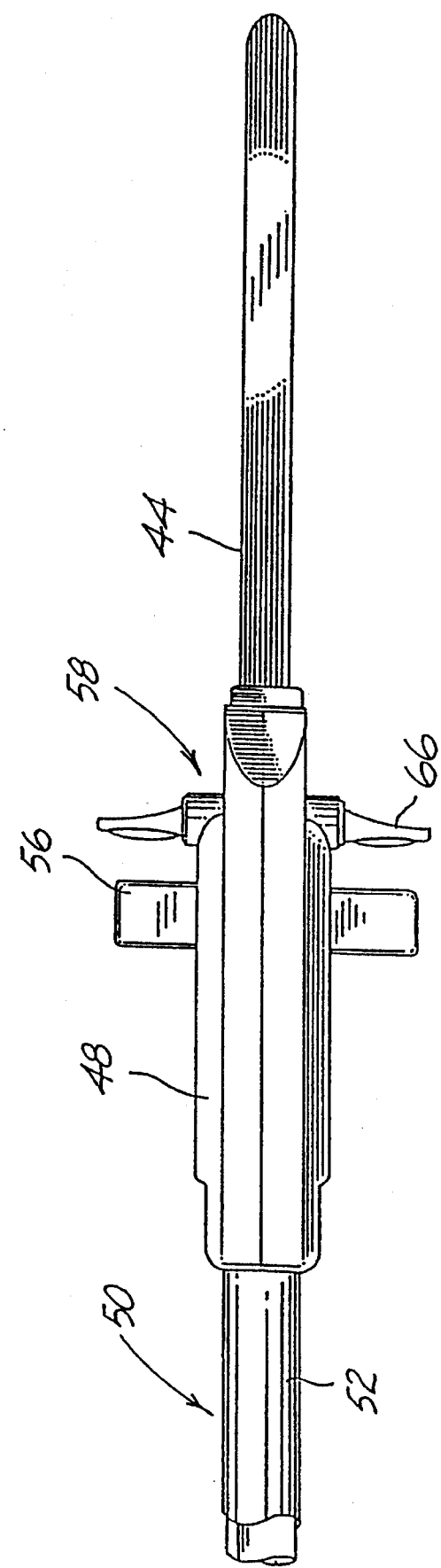
FIG. 8 illustrates a top plan view of the device of FIG. 6.

Ratchet mechanism 28 includes a pawl member 32 which engages a rack member 30 which is located on the pivoting handle 14. Rack member 30 comprises a plurality of indentations or notches which accepts pawl member 32 to hold pivoting handle 14 in place. Ratchet mechanism 28 utilizes an integrally constructed leaf spring member 34 which biases ratchet mechanism 28 into the engaged position such that pawl member 32 engages rack member 30. To release the ratchet mechanism, a trigger member 36 is provided which, when depressed by the user in the direction of arrow A in FIG. 3, causes the ratchet mechanism 28 to pivot about pivot point 38 in the direction of arrow B to disengage pawl member 32 from rack member 30. It can be appreciated that continual depression of trigger member 36 in the direction of arrow A allows the ratchet mechanism 28 to be overridden so that pivoting handle 14 may operate freely without the constraints of ratchet mechanism 28. Releasing trigger member 36 will return the pawl member 32 to the engaged position. Ratchet mechanism 28 can be best seen in FIGS. 4 and 5.

FIG. 6 illustrates a second embodiment of the surgical instrument employing the ratchet mechanism of the present invention. Instrument 40 is similar to instrument 10 described above and includes a handle portion 42 to which body assembly 50 is attached. Body assembly 50 terminates in a tool mechanism similar to that described above.

Handle assembly 42 comprises a pivoting handle 44, a stationary handle 46 and a barrel portion 48. Body assembly 50 comprises an outer tubular member 52 through which an inner rod member 54 coaxially passes in sliding arrangement. Movement of pivoting handle 44 causes inner rod member 54 to reciprocate within outer tube 52. Outer tube 52 is secured within barrel portion 48. As can be seen in FIG. 6 and FIG. 7, a rotation knob 56 may be provided, along with ratchet mechanism 58.

Figure 9:
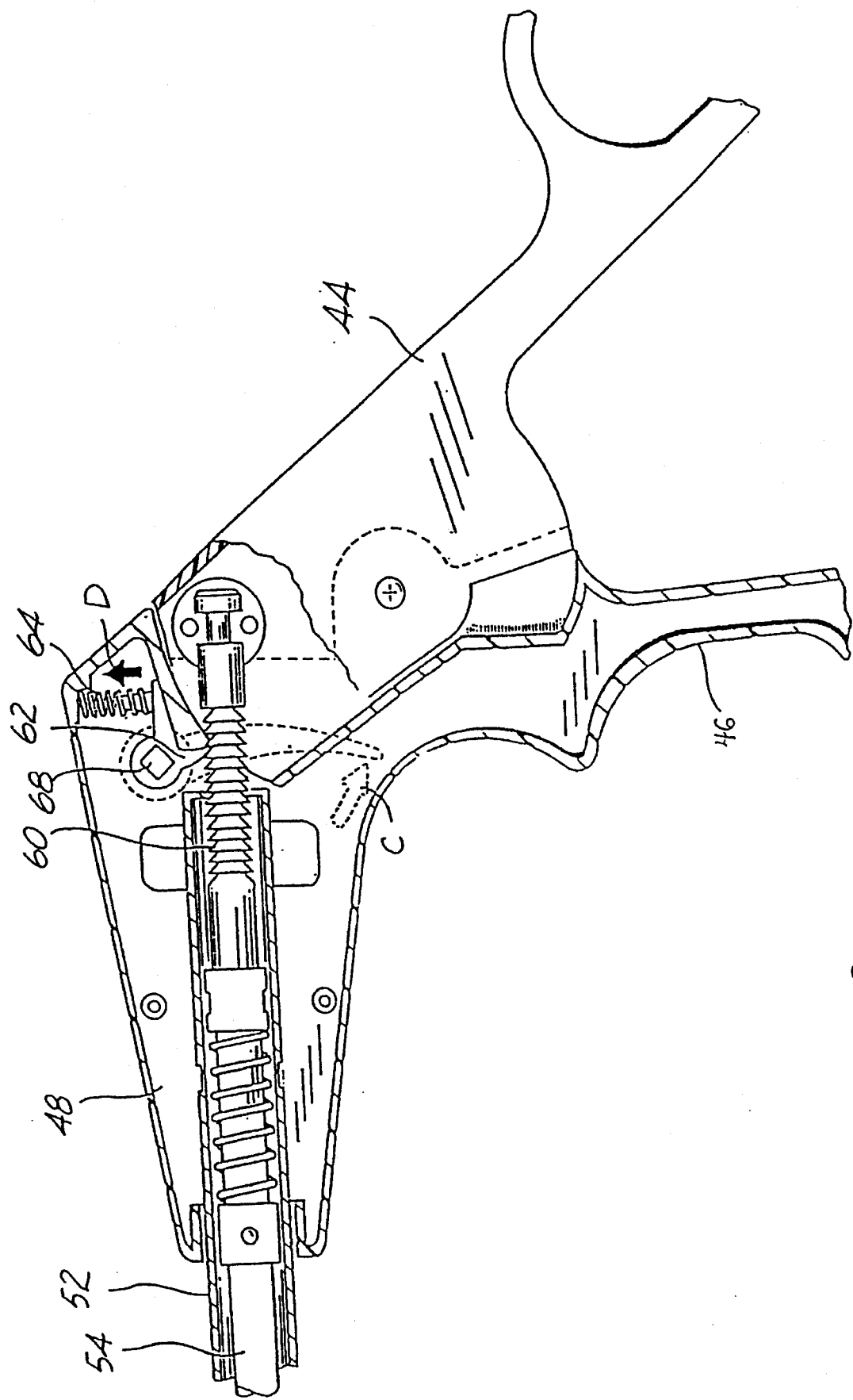
FIG. 9 illustrates a side cut-away view of the endoscopic or laparoscopic surgical instrument of FIG. 6 having the ratchet mechanism of the present invention.

FIG. 9 illustrates a cut-away view of the device of FIG. 6. Inner rod member 54 includes a rack member 60 which comprises a plurality of circumferential notches cut into rod member 54. The circumferential notches allow for activation of the ratchet mechanism at any orientation of the body assembly 50 due to rotation of rotation knob 56. While it is shown that rod member 54 contains the circumferential notches or indentations, a separate block member may be provided to which rod member 54 is attached to accomplish the same ratcheting principle.

Engaging rack member 60 is a pawl member 62 which is part of ratchet mechanism 58. Pawl member 62 is biased into the engaged position by spring 64, and is pivotable about pivot point 68.

In use, pivoting handle 44 is moved to open and close the jaw members of the tool mechanism (not shown). As pivoting handle 44 moves, pawl member 62 moves along rack member 60 to a desired location for the tool mechanism. To release ratchet mechanism 58, trigger member 66 is moved in the direction of phantom arrow C to overcome the spring force and move the pawl mechanism in the direction of arrow D. Once this mechanism is released, handle 44 is free to move without obstruction. In order to override the ratcheting mechanism, trigger member may be continually depressed in the direction of phantom arrow C so that the pivoting handle 44 may operate freely.

Figure 10:
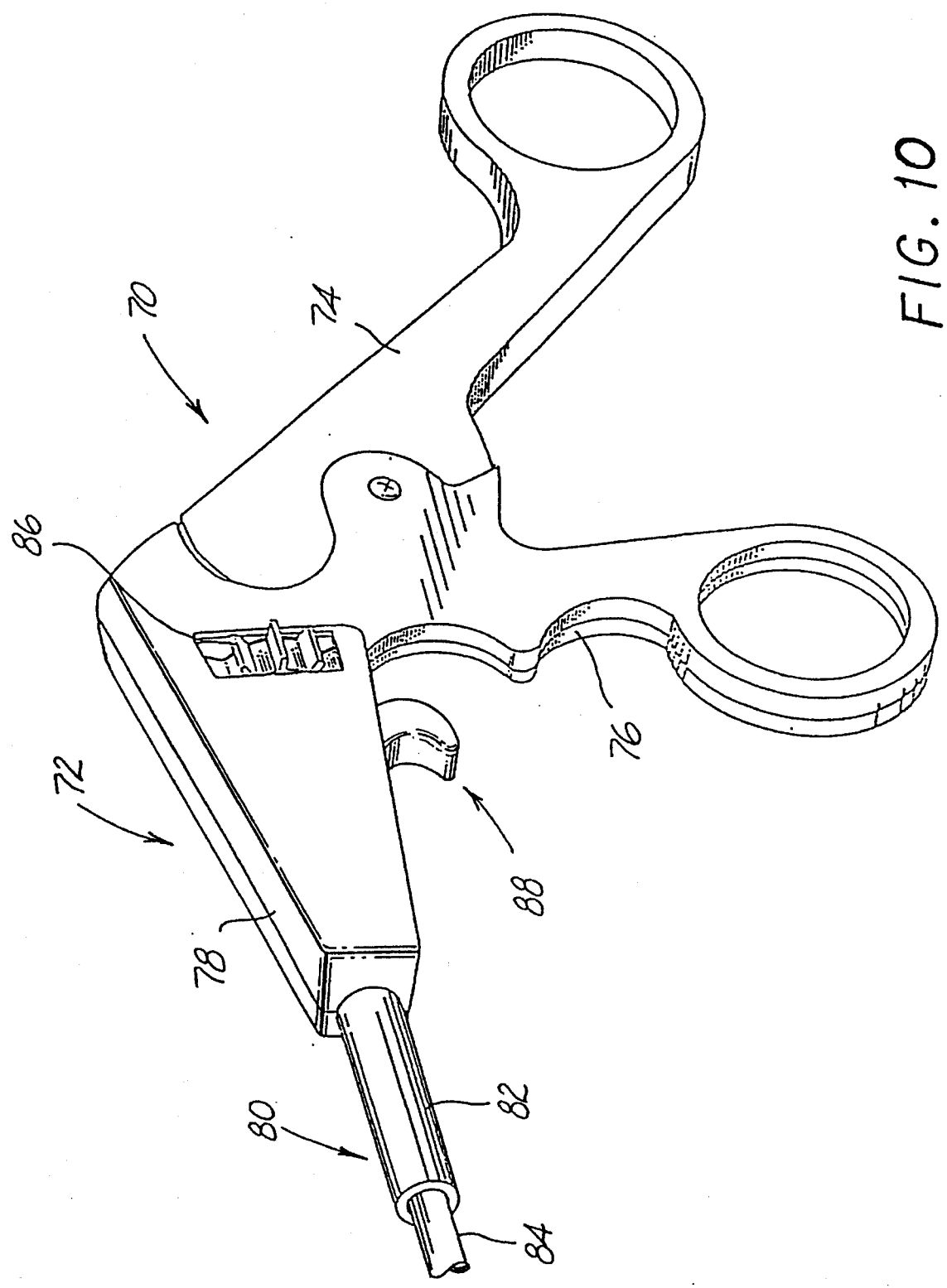
FIG. 10 illustrates a further embodiment of the endoscopic or laparoscopic surgical instrument employing the ratchet mechanism of the present invention.
Figure 11:
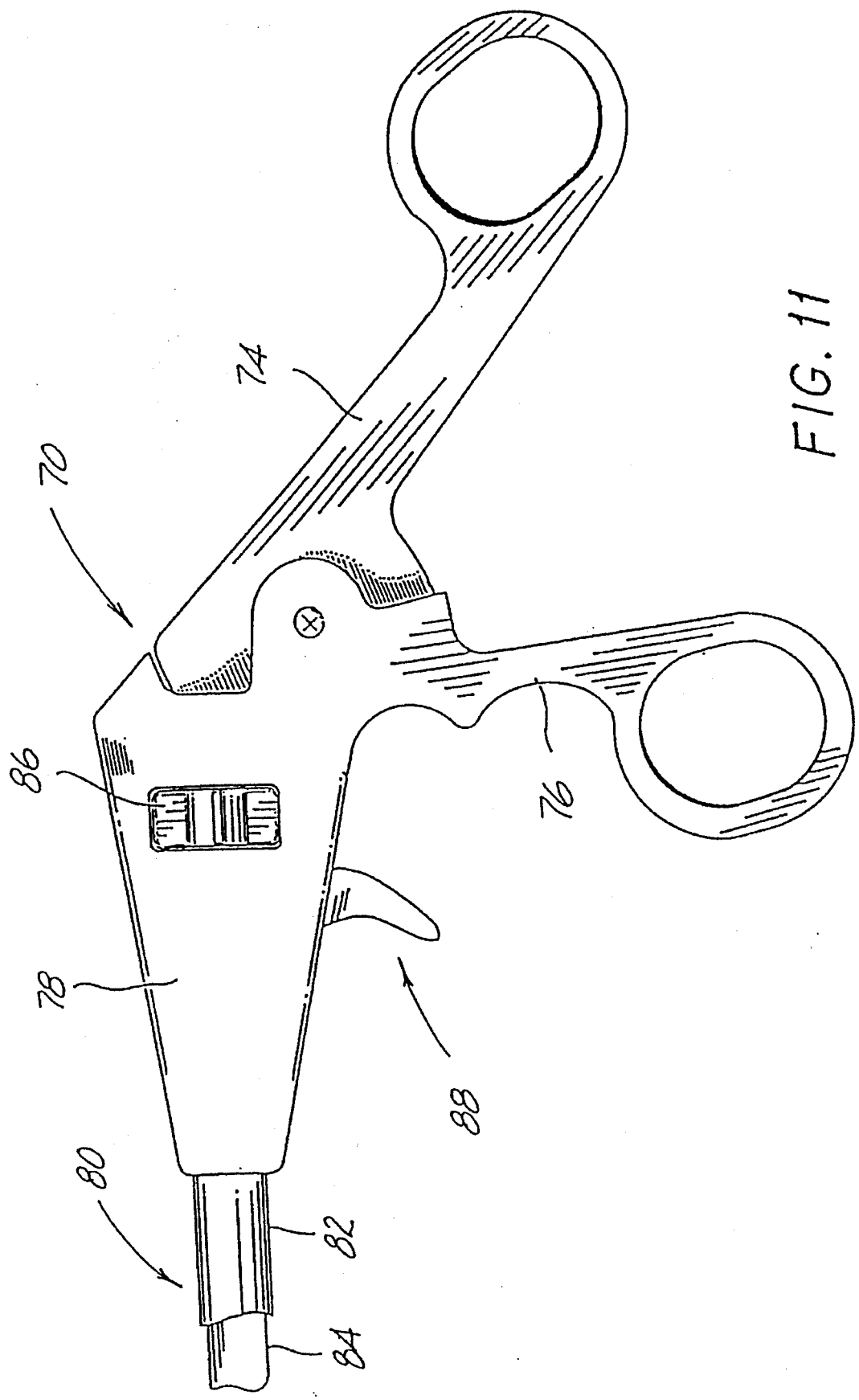
FIG. 11 illustrates a side view of the device of FIG. 10.

FIG. 10 illustrates a third embodiment of the endoscopic or laparoscopic surgical instrument employing the ratchet mechanism of the present invention. Instrument 70 is similar to devices 10 and 40 above and includes a handle assembly 72 and a body assembly 80. Body assembly 80 terminates in a tool mechanism similar to that described above. Handle assembly 72 includes a pivoting handle 74, a stationary handle 76 and a barrel portion 78. Body assembly 80 includes an outer tube member 82 which is secured to barrel portion 78, and an inner rod member 84 which coaxially passes through outer tube member 82 in sliding arrangement. Inner rod 84 reciprocates within outer tube member 82 upon movement of pivoting handle 74. A rotation knob 86 may be provided, and ratchet mechanism 88 is provided as a trigger grip extending from barrel portion 78.

Figure 12:
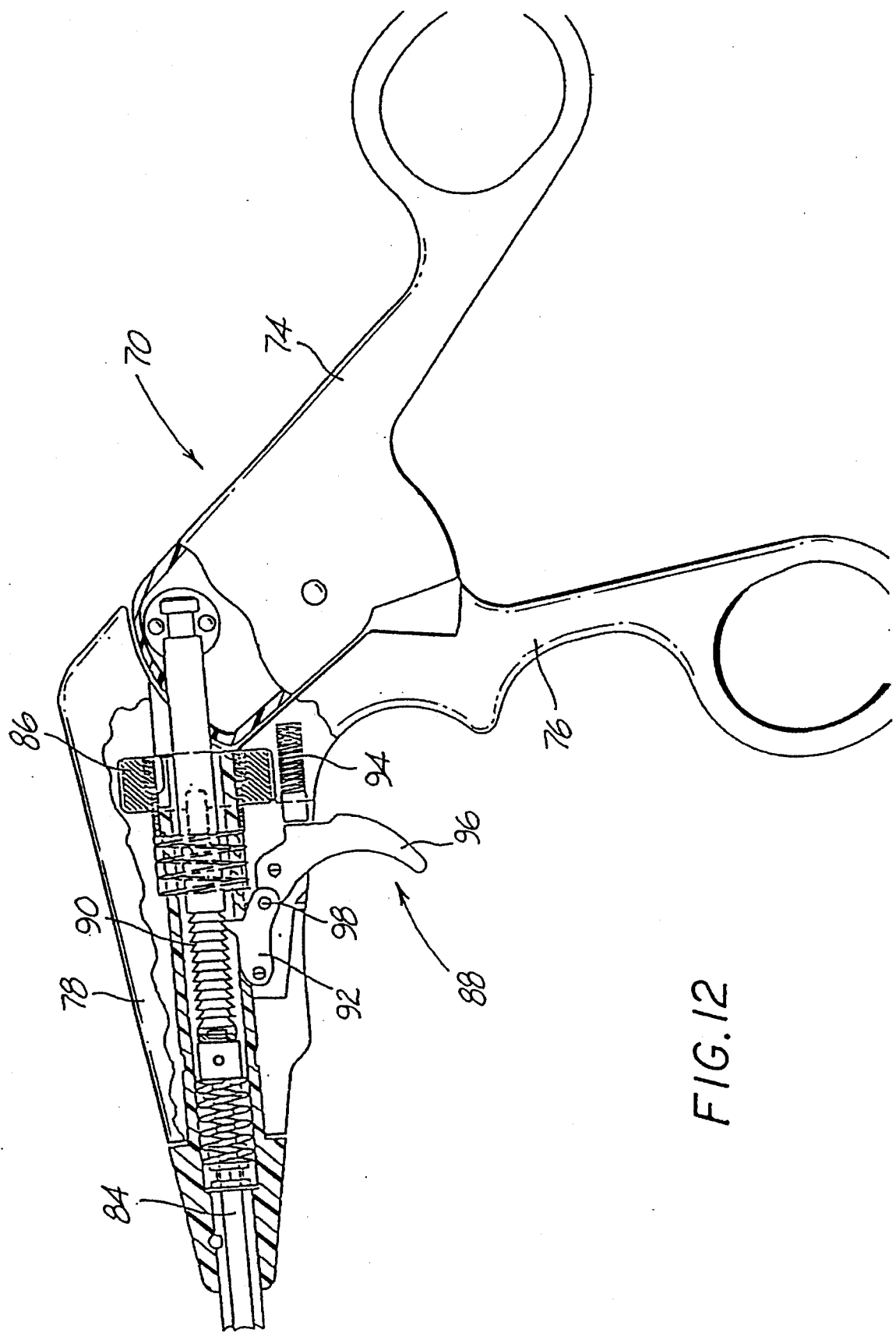
FIG. 12 illustrates a side cut-away view of the device of FIG. 10.

Turning to FIG. 12, there is illustrated the ratchet mechanism 88 which is disposed within barrel portion 78. A rack member 90 is provided which comprises a plurality of circumferential notches or indentations in inner rod member 84 which provide for engagement of the ratchet mechanism 88 regardless of the orientation of the tool mechanism due to rotation of rotation knob 86.

In this embodiment, ratchet mechanism 88 essentially comprises an articulated body which is comprised of pawl member 92 and trigger member 96. Trigger member 96 is biased by spring 94 which maintains pawl member 92 in engagement with rack member 90. The articulated body is formed about floating pivot point 98 which joins pawl member 92 with trigger member 96. Both the pawl member 92 and trigger member 96 are each secured at stationary pivot points while floating pivot point 98 allows pawl member 92 to move into and out of engagement with rack member 90.

In use, pivoting handle 74 is moved to set the jaws of the tool mechanism (not shown) to the desired configuration. Spring member 94 biases trigger member 96 forwardly, so that floating pivot point 98 urges pawl member 92 into engagement with rack means 90. To release the ratchet mechanism, trigger member 96 is urged rearwardly against the biasing force of spring 94 so that floating pivot point 98 shifts downwardly to move pawl member 92 out of engagement with rack means 90. Maintaining this rearward depression of trigger member 96 will provide an override for the ratchet mechanism 88, and allow pivoting handle 74 to move freely.

Figure 13:
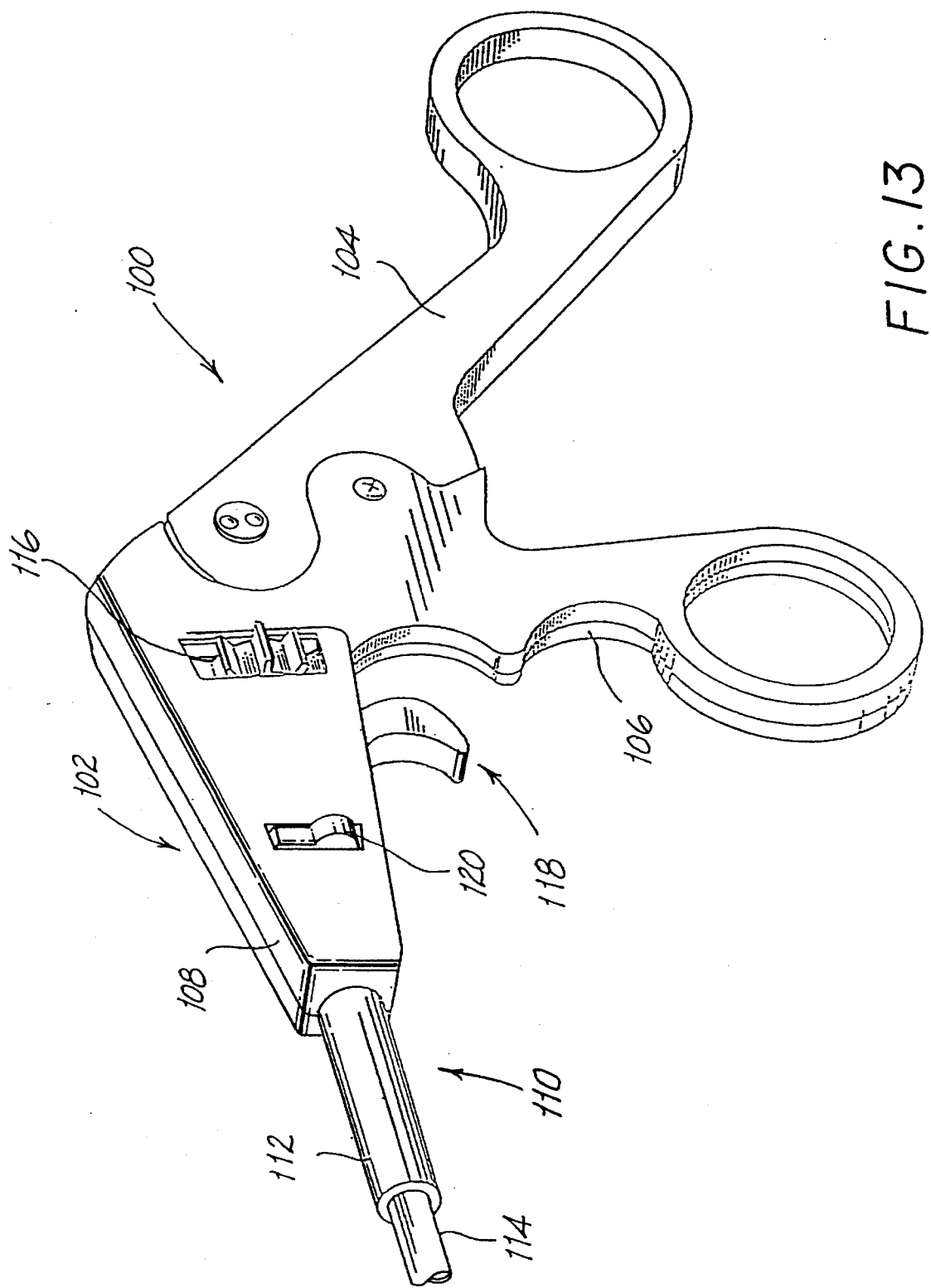
FIG. 13 illustrates another embodiment of the endoscopic or laparoscopic surgical instrument employing the ratchet mechanism of the present invention.

FIG. 13 illustrates a fourth embodiment of the endoscopic or laparoscopic surgical instrument 100 employing the ratchet mechanism of the present invention. Instrument 100 is similar to instruments 10, 40 and 70 above, and includes a handle assembly 102, a body assembly 110, and a ratchet mechanism 118. Handle assembly 102 comprises a pivoting handle 104, a stationary handle 106 and a barrel portion 108, to which body assembly 110 is secured. Body assembly 110 comprises an outer tubular member 112 and a coaxial inner rod member 114 which slides therein. Outer tube member 112 is secured to barrel portion 108, while inner rod member 114 is secured to pivoting handle 104 and reciprocates within outer tube member 112 upon movement of pivoting handle 104. A rotation knob 116 is provided to adjust the orientation of the tool mechanism (not shown) which is located at the distal end of the body assembly 110. Ratchet mechanism 118 is provided, along with actuation means 120, whose function will be described below.

Figure 15:
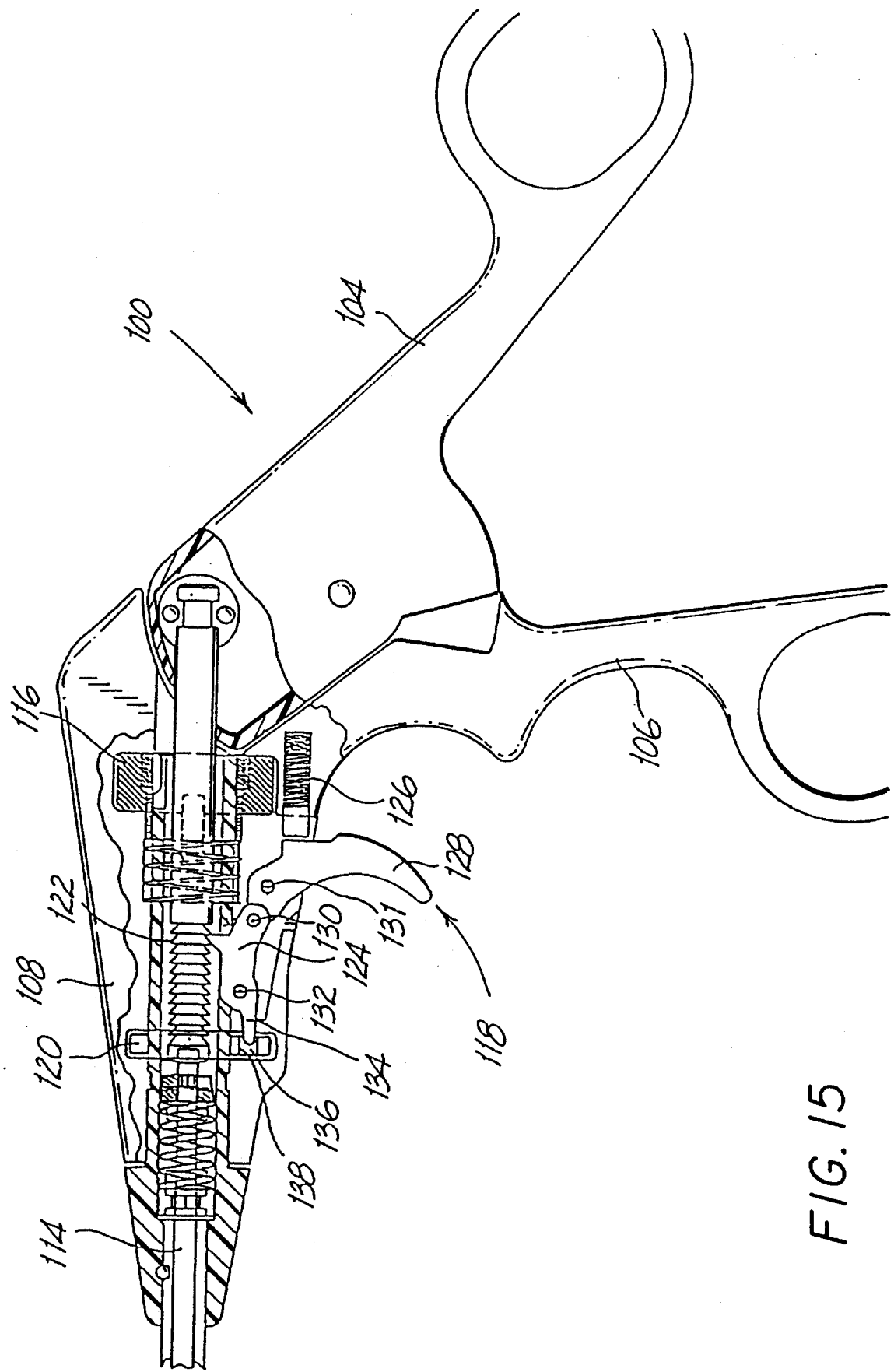
FIG. 15 illustrates a side cut-away view of the device of FIG. 13.

Turning now to FIG. 15, there is illustrated a side cutaway view of instrument 100 showing the ratchet mechanism 118 of the present invention. Inner rod member 114 includes a rack member 122 which comprises a plurality of circumferential notches or indentations which allows for use of the ratchet mechanism 118 regardless of the orientation of the tool mechanism due to rotation of body assembly 110 by rotation knob 116. Ratchet mechanism 118 comprises an articulated body which is formed by pawl member 124, trigger member 128 and a camming member 134 which extends from pawl member 124. Trigger member 128 pivots about a stationary pivot point 131 and is biased in the forward direction by spring 126. Trigger member 128 is joined to pawl member 124 through floating pivot point 130, while pawl member 124 is pivoted further about stationary pivot point 132.

Figure 19:
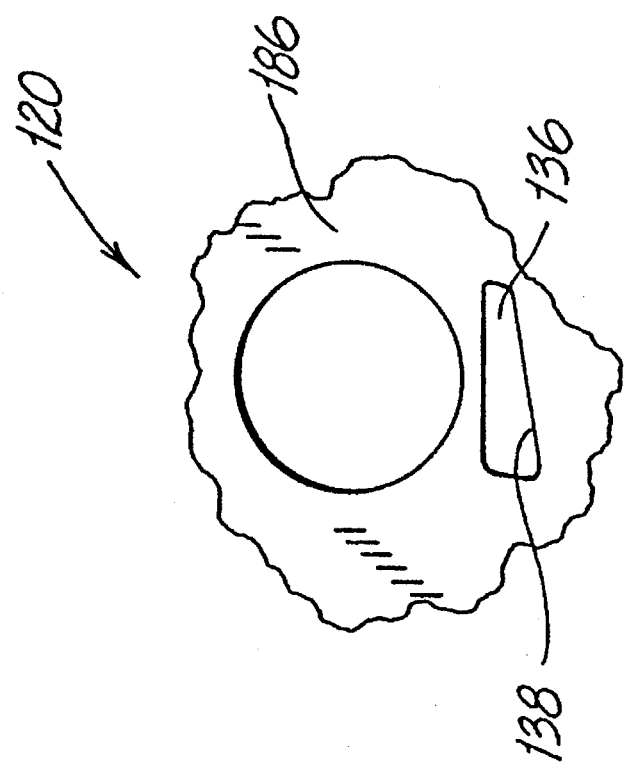
FIG. 19 illustrates a plan view of an embodiment of the actuation means for use with the ratchet mechanism of the present invention.
Figure 26:
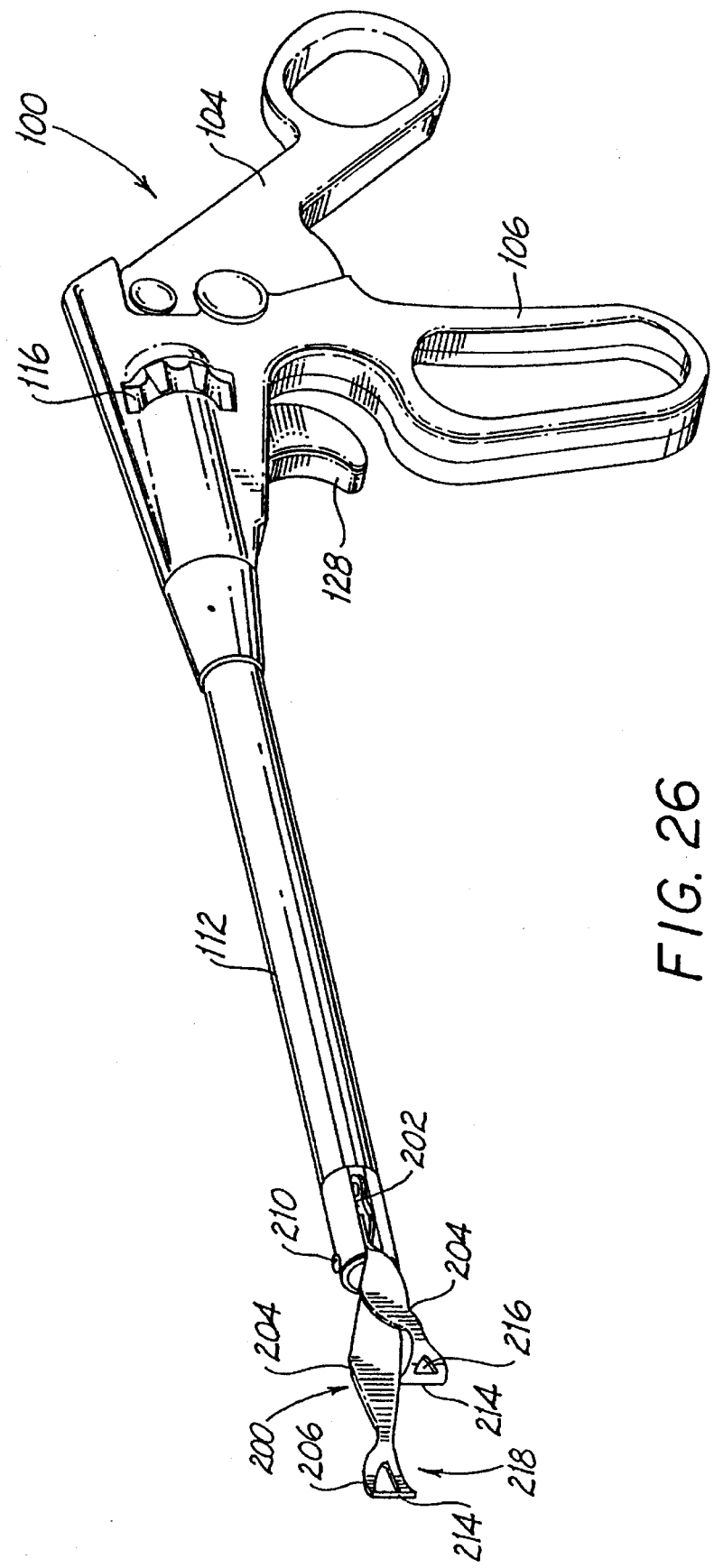
FIG. 26 illustrates a perspective view of an endoscopic instrument incorporating the jaw mechanism of FIG. 24.

An actuation means 120 is provided, which is best seen in FIG. 19. Actuation means 120 comprises a body portion 186 and is provided with a camming slot 136 into which camming member 134 passes. Camming surface 138 engages camming member 134 to urge pawl member 124 into engagement with rack member 122. When actuation means 120 is pushed in a first direction, camming member 134 disengages from camming surface 138 and pawl member 124 disengages from rack member 122. When actuation means 120 is pushed in the opposite direction, camming surface 138 contacts camming member 134 which urges pawl member 124 into engagement with rack member 122. Actuation means 120 functions as a switch to the user to override the ratchet mechanism so that the device 100 may be used in a conventional manner without requiring the user to hold any component of the instrument.

Figure 14:
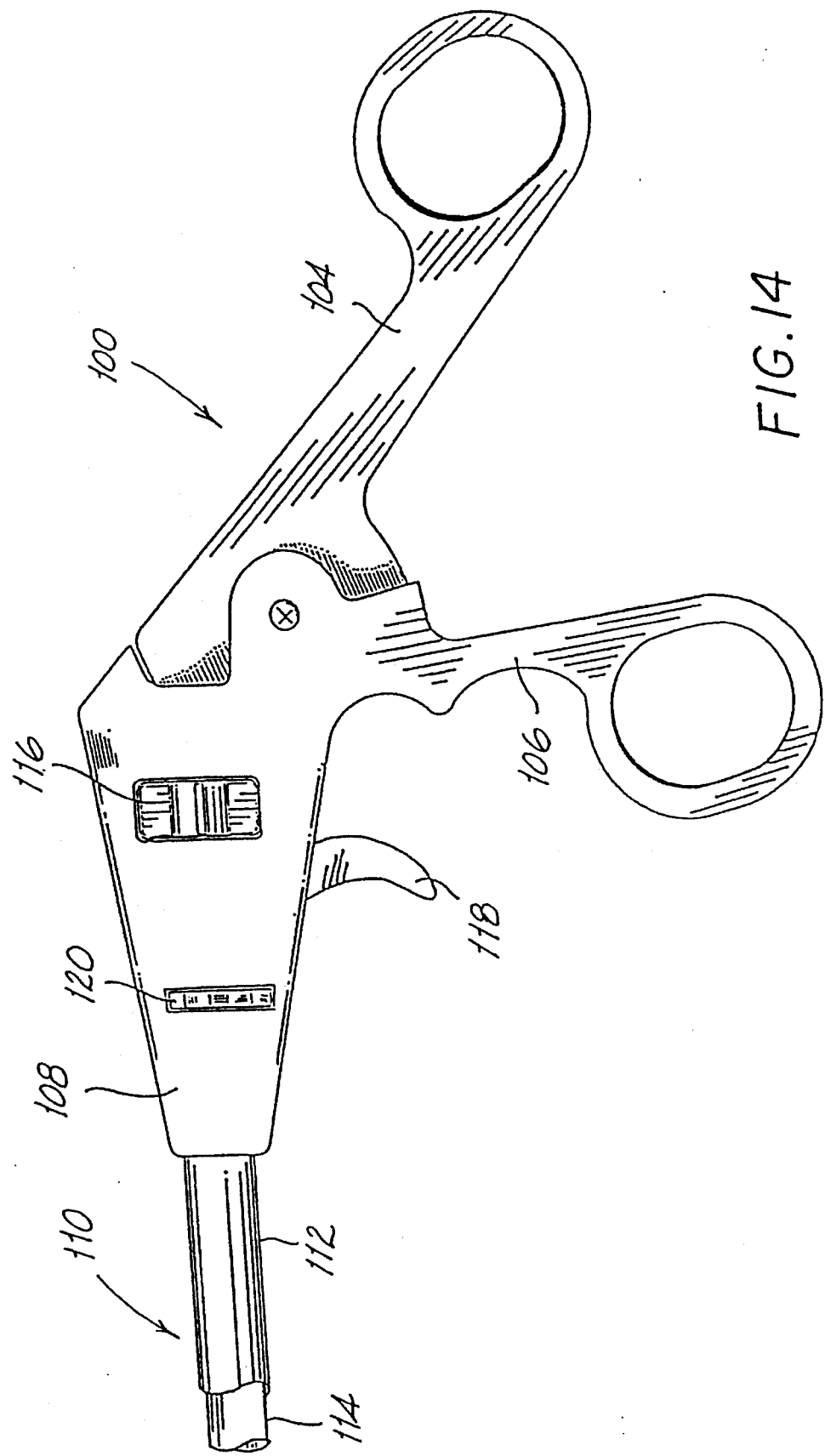
FIG. 14 illustrates a side plan view of the device of FIG. 13.
Figure 16:
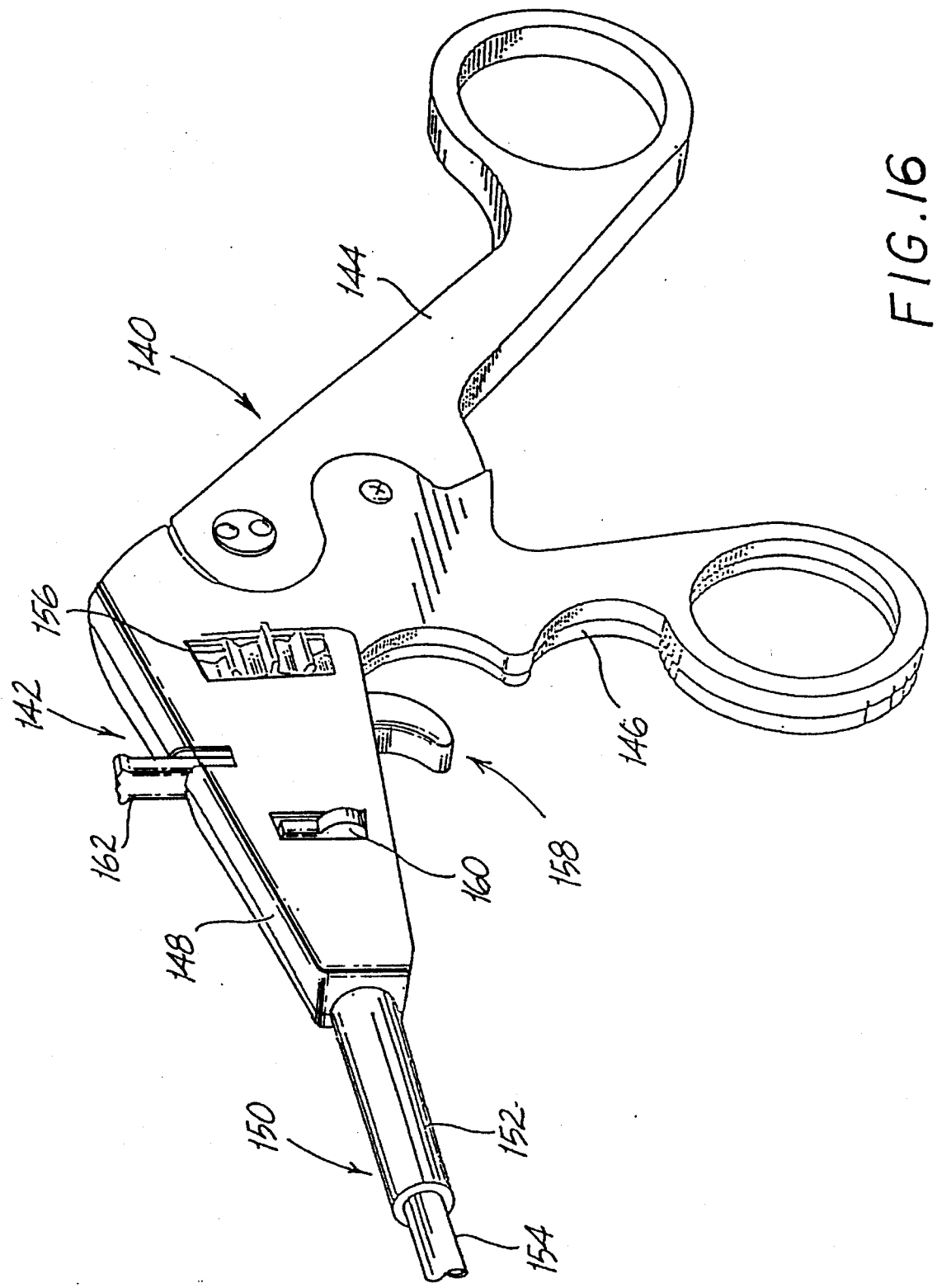
FIG. 16 illustrates a perspective view of a further embodiment of the endoscopic or laparoscopic surgical instrument employing the ratchet mechanism of the present invention.
Figure 17:
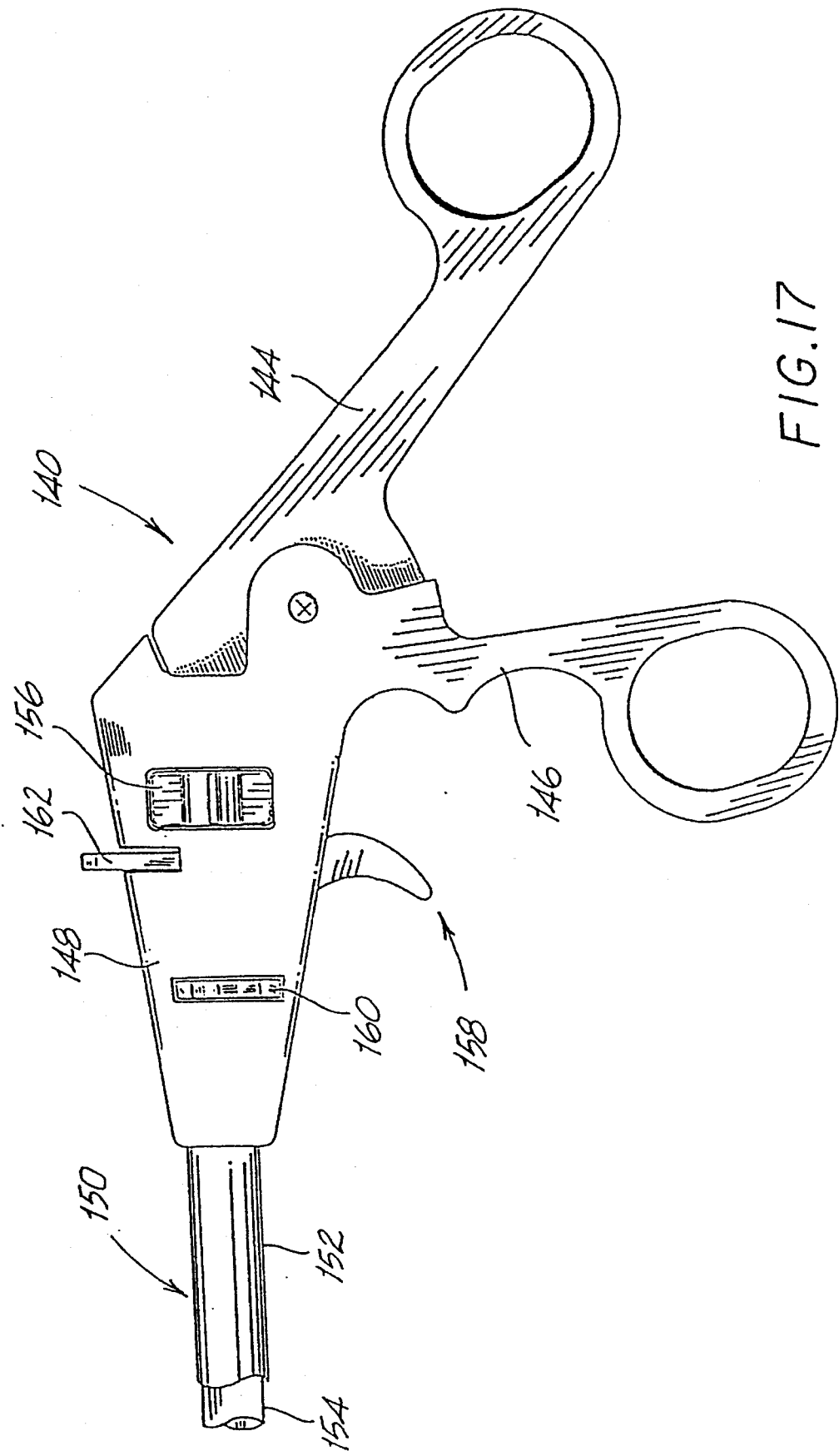
FIG. 17 illustrates a side plan view of the device of FIG. 16.

FIG. 16 illustrates a fifth embodiment of the endoscopic or laparoscopic surgical instrument 140 employing the ratchet mechanism of the present invention. Device 140 is identical to device 100 described above in relation to FIGS. 13–15, except for the provision of rotation stop means 162.

Instrument 140 comprises handle assembly 142, body assembly 150, and ratchet mechanism 158. Handle assembly 142 comprises pivoting handle 144, stationary handle 146, and barrel portion 148. Body assembly 150 attaches to barrel portion 148 in the manner described above, such that outer tube member 152 is secured to barrel portion 158 while inner rod member 154 slidingly passes through tube member 152 and is secured to pivoting handle 144. Inner rod member 154 reciprocates within outer tube member 152 in response to movement of pivoting handle 144. A rotation knob 156 is provided, along with actuation means 160 which cooperates with ratchet mechanism 158 as described above.

Figure 18:
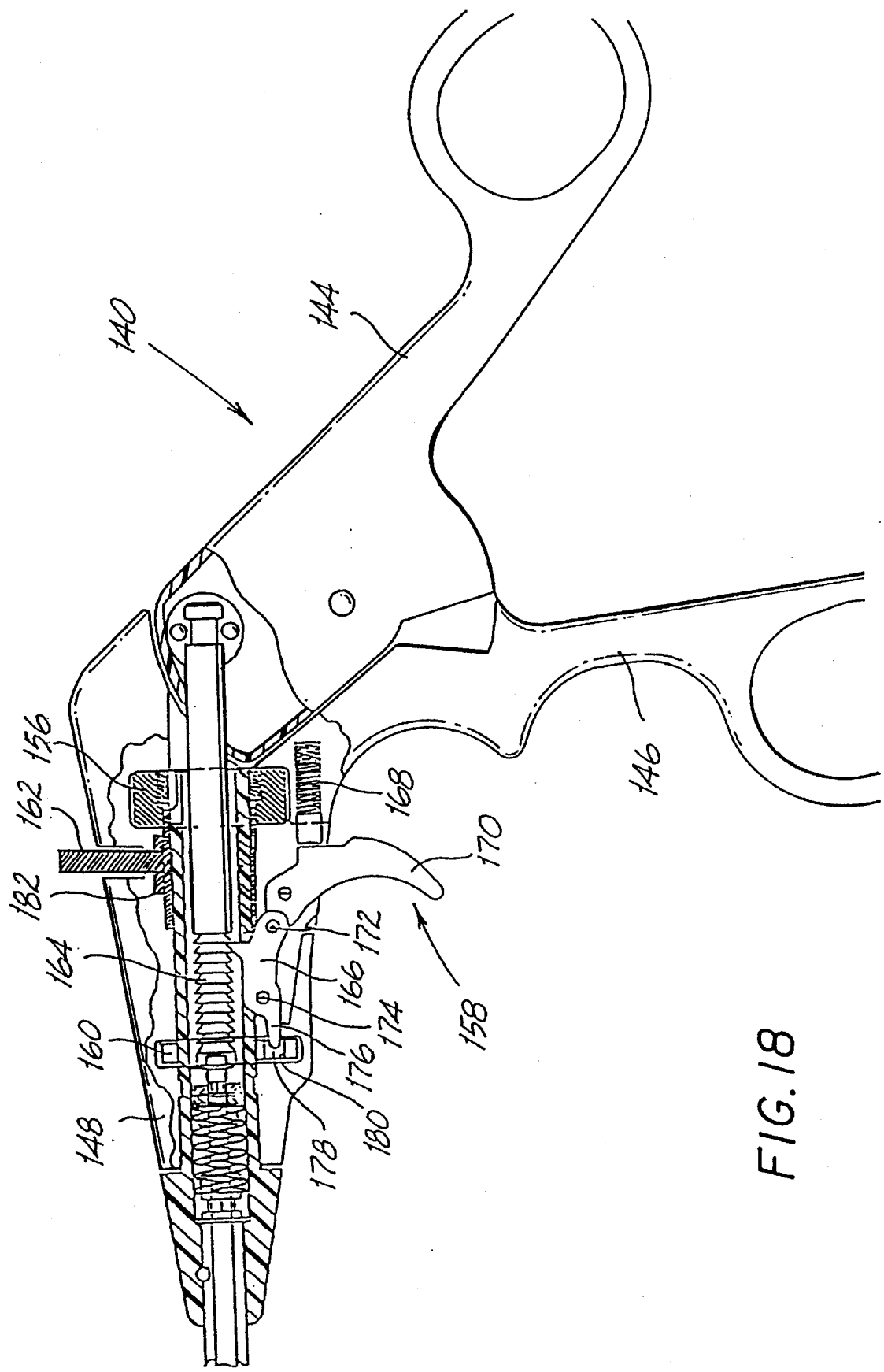
FIG. 18 illustrates a side cut-away view of the device of FIG. 16.
Figure 20:
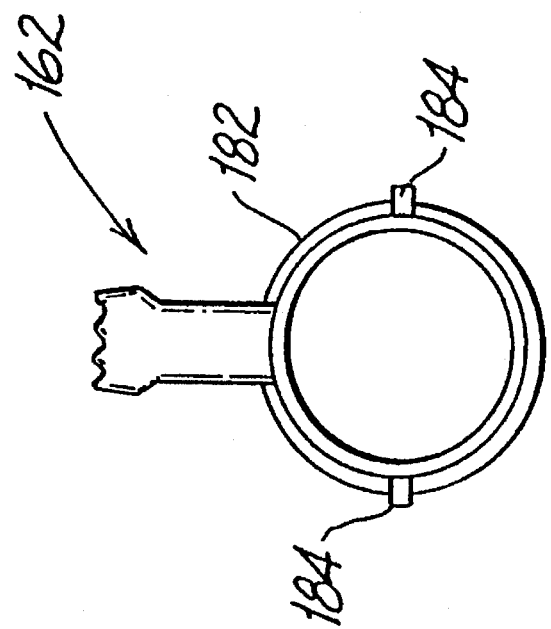
FIG. 20 illustrates a plan view of the stop means for use with the rotation knob of the present invention.

Turning now to FIG. 18, and in view of FIG. 20, ratchet mechanism 158 and actuation means 160 operate in a manner identical to that described above in reference to FIGS. 13–15. Stop means 162 is provided having a body portion 182 surrounding outer tube member 152. Rotation of rotation knob 156 allows for various orientations of the tool mechanism (not shown) which is provided at the distal end of body assembly 150. In order to secure body assembly 150 at a particular orientation, stop means 162 is provided which frictionally engages outer tubular member 152 to lock it in place at the desired orientation. The friction force is applied upon rotation of stop means 162 through the provision of guide posts 184 which travel in tracks provided in barrel portion 148. Guide posts 184 provide a torque to body portion 182 which grips outer tubular member 152 to arrest rotational movement at the desired orientation.

Embodiments of the present invention may further include novel tool mechanisms in the form of atraumatic jaw mechanisms having jaw members with flexural characteristics. These jaw members are capable of transmitting to users a more accurate "feel" so that they can gauge the amount of force being applied to the captured tissue by the instrument. In particularly advantageous embodiments, these jaw members may be fabricated using a unique manufacturing technique which eliminates or substantially reduces the need for elaborate and expensive metal working equipment.

Referring to FIGS. 21–26 and in particular to FIGS. 21–23, a novel jaw member and method of manufacturing same is illustrated. This jaw member is shown in the form of a Babcock clamp jaw 200 adapted to capture and hold tubular tissue, preferably without causing traumatic injury. Babcock clamp jaw 200 comprises a proximal portion 202, an intermediate portion 204 and a distal portion 206.

As shown in FIG. 21, the proximal portion 202 of the Babcock clamp jaw 200 is provided with a pivot bore 208 transversely formed therein for receiving a pivot pin 210 (FIG. 24) to interconnect a pair of jaw members. Proximal portion 202 further includes means for moving the interconnected jaw members pivotally relative to one another. In the embodiment shown in FIGS. 21–26, this structure comprises a diagonal camming slot 212 formed in the proximal portion 202, which slot receives a camming pin 24 connected to and controlled by inner rod member 114. Note that the present novel jaw structure is described in the context of a surgical instrument in accordance with the embodiment of FIG. 15 discussed hereinabove. However, the jaw structure of the present invention may be equally incorporated into other surgical instrument configurations including the alternative embodiments discussed herein.

The distal portion 206 of the Babcock clamp jaw 200 includes a contact surface 214 and a tissue expansion bore 216 formed therein. Tissue expansion bore 216 also provides a fluid passage for fluids associated with grasped tissue. The distal portion is formed into a substantially semicircular shape defining a tissue capturing space 218 on an interior surface thereof.

Intermediate portion 204 is disposed between proximal portion 202 and distal portion 206 and permits the distal portion 206 to flex transversely with respect to proximal portion 202 when the contact surface 214 of two opposing clamp jaw members contact or when an enlarged tissue structure is contained within tissue capturing space 218. In the embodiment of FIGS. 21–26, the distal portions 206 of clamp jaw member 200 are precambered inward such that as the opposing Claim jaws are approximated, the contact surface 214 of the respective distal portions 206 come into abutment first. This configuration allows the intermediate portion 204 to flex or bend thus transmitting a feel to the user of the force being applied.

The Babcock clamp jaws 200 may advantageously be formed in a novel manner from a single sheet of material. Preferably, this material is relatively strong and malleable with good flexural characteristics, e.g. Series 302 or 304 stainless steel.

To form the jaws, the basic shape of the jaw is stamped or formed out of a single flat sheet of material. Thereafter, any desired bores or slots may be formed as desired. Once the basic flat shape is present, the distal end of the flattened workpiece is twisted or bent so that the distal end is disposed in a predetermined angular orientation with respect to the proximal portion of the workpiece. In the embodiment of FIGS. 21–26, the distal portion 206 is twisted in the direction of arrow 220 (FIG. 22) until the distal portion 206 is disposed in a plane approximately 90° transverse to the plane of the proximal portion 202.

Once the workpiece is bent into the correct shape, the distal portion 206 of the jaw member 200 is formed into its final semicircular shape using, for example, a dowel or other forming tool of a predetermined shape. See FIG. 23. The distal portion may also be precambered to provide a larger range of flexibility for the jaw members.

The embodiment of FIGS. 21–26 demonstrate jaw members wherein the distal portions thereof are each bent in the same transverse direction relative to the respective proximal portions. This advantageous configuration permits the jaws, when assembled together to overlap and minimize visual obstruction of the tissue capturing area 218.

Referring to FIG. 24, opposing Babcock clamp jaws 200 are disposed in a closed approximated position with intermediate portions 204 overlapping and contact surfaces 214 in abutment. This position facilitates insertion of the instrument 222 through a cannula (not shown). Once in place within the endoscopic operative site, the ratcheting mechanism 118 (FIG. 15) is released by means of trigger 128 allowing Babcock clamp jaws 200 to spring open in preparation for tissue capture. The subject tissue (not shown) is maneuvered into the tissue capturing space 218 and the jaws 200 are reapproximated using pivoting handle 104 and stationary handle 106 to retract coaxial inner rod member 114 relative to outer tube member 112. As the contact surfaces 214 of the distal portions 206 abut, the user may effectively gauge the application of more force to the captured tissue as the distal portion of the jaws flex via the intermediate portion relative to the proximal portion.

FIGS. 27–31 illustrate a further embodiment of Babcock clamp jaws 230 in accordance with the present invention. These jaws 230 are substantially the same as Babcock clamp jaws 200 discussed above with the exception of the linkage means 232 used to connect the jaws 200 to the inner rod 114 and activate the jaws to pivotally move them between an open position (FIG. 31) and a closed position (FIG. 30).

The jaws 230 include a proximal portion 234, an intermediate portion 236 and a distal portion 238. The proximal portion 234 includes a pivot bore 208 for receiving pivot pin 210 and a link pin bore 240 for receiving link pin 242 to connect the jaw 230 to articulating link 244. Links 244 of opposing jaws 230 are connected to coaxial inner rod member 114 at pin 246, and serve to drive the jaws 230 between an open and closed position as the rod member 114 is moved coaxially with respect to outer tube member 112.

The intermediate portion 236 is substantially the same as intermediate portion 204 of FIGS. 21–26 and has flexural characteristics which allow distal portion 238 to flex relative to proximal portion 234.

The distal portion 238 is solid and terminates in a more aggressive contact surface 248 provided with interdigitating teeth 250. As in the previous embodiment, the distal portion is precambered inwardly so that as the jaws 230 are approximated, the contact surface 248 of respective opposing jaws contact first, leaving a space separating said intermediate portions 236 to allow for flexing of the jaws 230 relative to one another.

Figure 32:
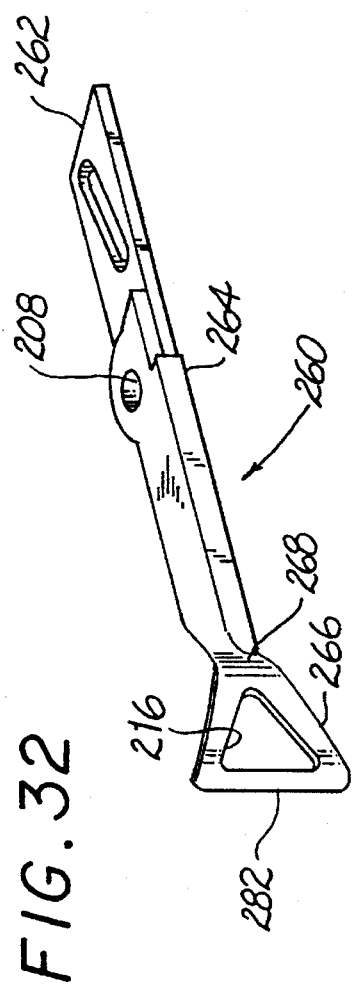
FIG. 32 illustrates a perspective view of a jaw member in accordance with another embodiment of the present invention.
Figure 33:
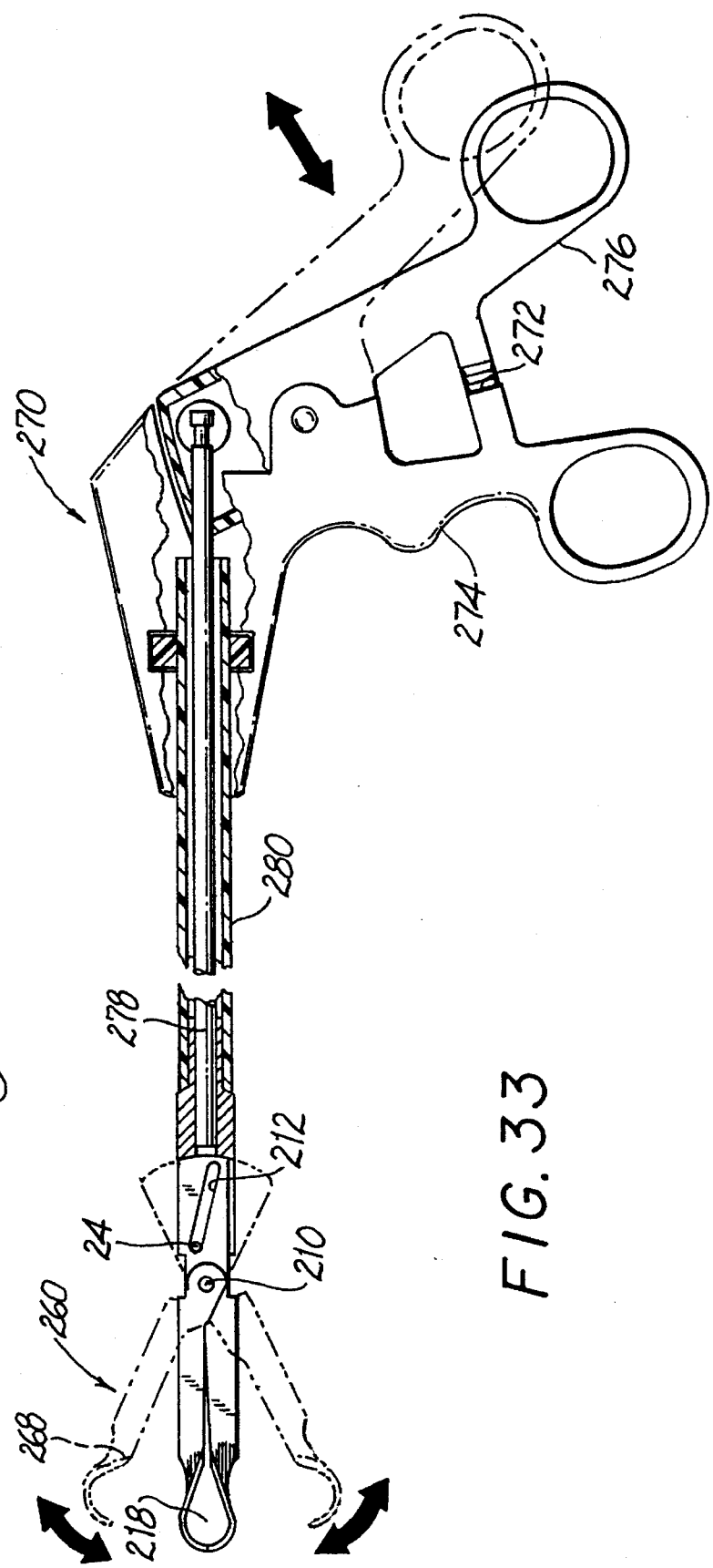
FIG. 33 illustrates a side plan view in cross section of an endoscopic instrument incorporating the jaw member of FIG. 32.

Turning now to FIGS. 32 and 33, there is illustrated a third configuration of the Babcock clamp jaw in accordance with the present invention. The clamp jaw 260 includes a proximal portion 262, an intermediate portion 264 and a distal portion 266. The proximal and distal portions of this embodiment of the Babcock clamp jaw 260 are formed in substantially the same configuration as the Babcock clamp jaw 200 disclosed above. The intermediate portion 264 is formed with the bend 268 located almost directly adjacent the near end of the distal portion 266 such that only a relatively small percentage of the jaw structure is disposed in the distal portion in a plane perpendicular to the plane of the proximal portion 262. This configuration allows for a longer intermediate portion 264 while maintaining adequate control and flexural characteristics Of the jaw 260. Also, the distal portions 266 of opposing jaw members 260 are formed or bent in correspondingly opposite transverse directions and do not substantially overlap as in jaws 200 and 230.

FIG. 33 shows an instrument 270 incorporating jaws 260 in conjunction with an external ratchet 272 disposed between the stationary handle 274 and the pivoting handle 276. In the open position (shown in phantom) camming pin 24 disposed in coaxial inner rod 278 is in its distal most position camming opposing jaws 260 apart. Compression of handles 274, 276 together causes inner rod 278 to retract relative to outer tube 280 camming the jaws 260 together such that contacting surfaces 282 of the distal portion 266 of jaw 260 come in contact. Further compression of the handles 274, 276 causes the distal portion 266 to flex relative to the proximal portion 262 through intermediate portion 264. The external ratchet 272 permits the jaws 260 to be locked in preselected degrees of closure and/or compression.

Figure 34:
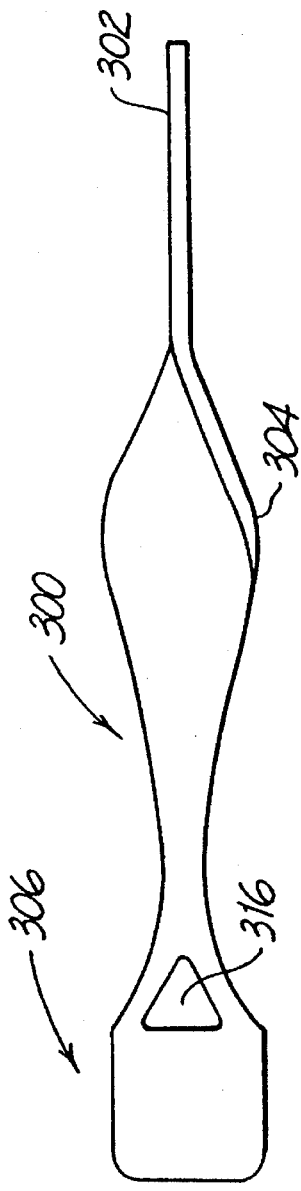
FIG. 34 illustrates a top view of a jaw member in accordance with one embodiment of the present invention prior to being formed.
Figure 35:
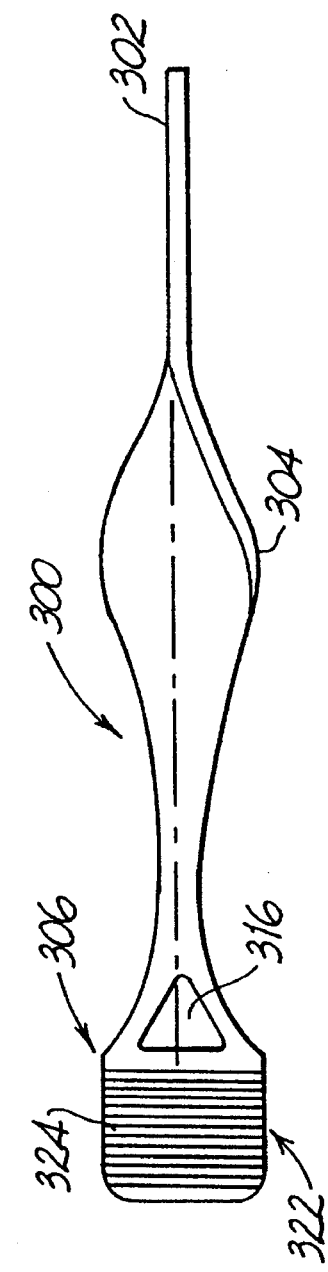
FIG. 35 illustrates a bottom view of the jaw member of FIG. 34 wherein a proximal end is bent relative to the distal end.
Figure 36:
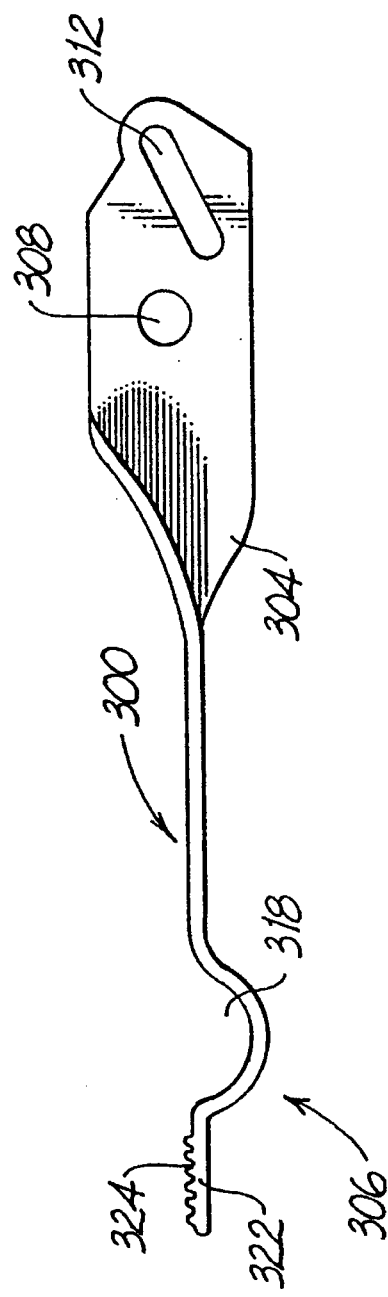
FIG. 36 illustrates a side plan view of the jaw member of FIG. 35 wherein the distal end is formed having a semicircular configuration and a serrated portion extending distally therefrom.
Figure 37:
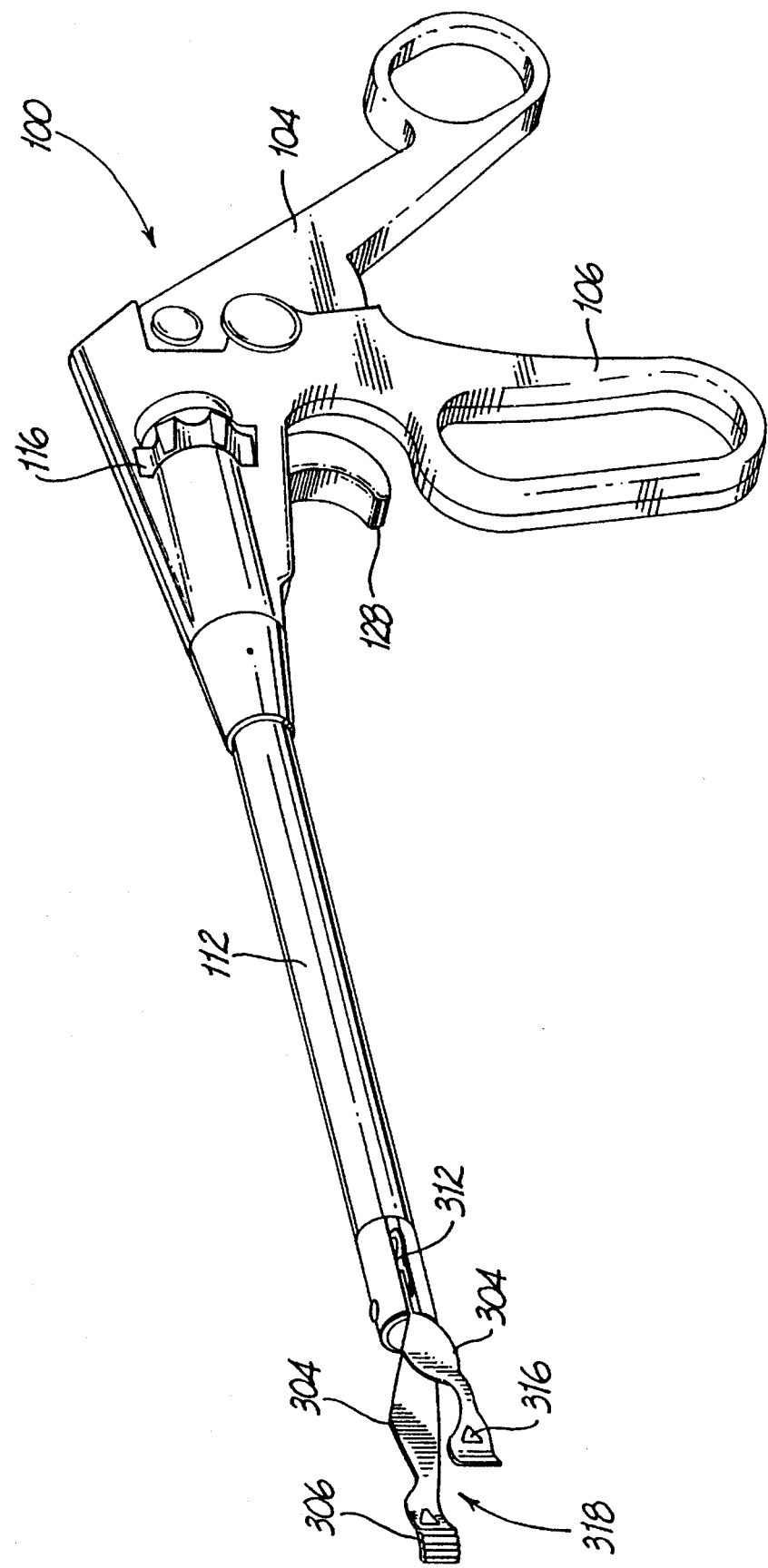
FIG. 37 illustrates a perspective view of an endoscopic instrument utilizing the jaw member of FIG. 36.

Referring to FIGS. 34–38 and in particular to FIGS. 34–36, a further novel jaw member embodiment is illustrated. The jaw member is shown in the form of a Babcock clamp and tissue gripper jaw 300 adapted to optionally capture and hold tubular tissue, preferably without causing traumatic injury, or firmly grip tissue. Babcock clamp and tissue gripper jaw 300 comprises a proximal portion 302, an intermediate portion 304 and a distal portion 306. Proximal portion 302 and intermediate portion 304 are similar to the corresponding elements as described for FIGS. 21–23 above and will not be discussed further herein.

Distal portion 306 of babcock clamp and tissue gripper jaw 300 includes tissue expansion bore 316 formed therein. Tissue expansion bore 316 also provides a fluid passage for fluids associated with tissue grasped in tissue capturing space 318 on an interior surface of distal portion 306. Tissue gripping face 322 extends distally away from tissue capturing space 318 and has teeth 324 disposed transversely along tissue gripping face 322. Alternatively, longitudinally extending teeth could be provided.

The embodiment of FIGS. 34–37 illustrate jaw members wherein the distal portions thereof are each bent in the same transverse direction relative to the respective proximal portions. This advantageous configuration permits the jaws, when assembled together, to overlap and minimize visual obstruction of the tissue capturing area 318. The operation of babcock clamp and tissue gripper jaw 300 is similar to that described above for FIGS. 21–26, however, the addition of novel tissue gripping face 322 provides additional gripping surface and the further capability of jaw 300 to grasp tissue between tissue gripping faces 322 on opposing jaw members without requiring a separate instrument. This feature provides surgeons with additional gripping surface on the same instrument and allows them to perform multiple functions with the same instrument thereby eliminating the need for additional trocars and access points for additional instruments to the surgical site. Excess instrumentation is, therefore, avoided and the operating area is not unnecessarily cluttered with instrumentation and the associated packaging.

Figure 38:
FIG. 38 illustrates a partial side view of the distal end of a jaw member in accordance with another embodiment of the present invention.
Figure 39:
FIG. 39 illustrates a partial side view of the distal end of a jaw member in accordance with another embodiment of the present invention.

Referring to FIGS. 38 and 39, babcock clamp and tissue gripper jaws 340 and 350 are shown featuring alternative tissue gripping faces 342 and 352 having teeth 344 and 354, respectively disposed thereon. Babcock clamp and tissue gripper jaw 340 is rounded at distalmost end 346 while babcock clamp and tissue gripper jaw 350 has bulbous portion 356 extending downwardly away from teeth 354 for preventing extraneous tissue from being gripped between opposing tissue gripping portions 352. Bulbous portion 356 also reduces the risk of traumatic injury to the surrounding tissue during manipulation of the instrument.

Figure 40:
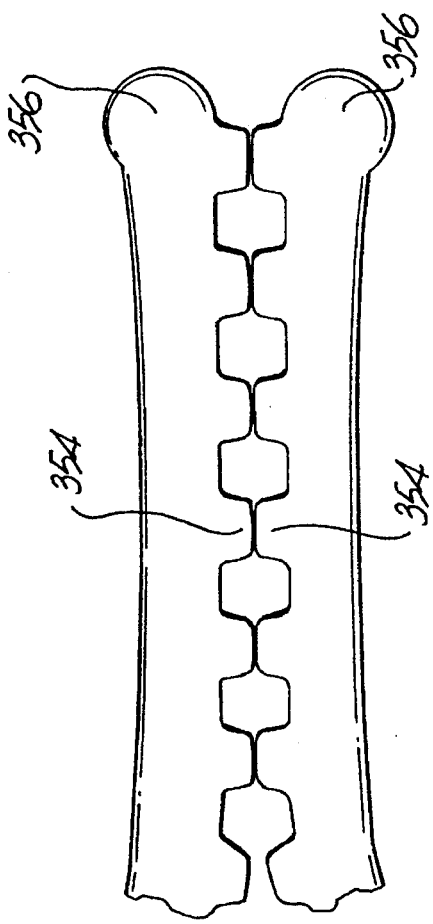
FIG. 40 illustrates a partial side view of the distal end of opposing jaw members having abutting teeth.

FIG. 40 shows one possible alignment of the jaw embodiment of FIG. 39 having opposing jaw members 350 biased so that teeth 354 abut to provide concentrated gripping forces at the planar contact points of abutting teeth 354. Alternatively, jaw members 350 or any of the other jaw embodiments disclosed herein could be configured such that teeth 354 mesh such that tissue gripped between opposing jaw members 350 would be compressed between the teeth and the corresponding gaps therebetween. In the embodiment illustrated in FIG. 40, teeth 354 have a truncated semicircular geometry with a flat top contact surface to maximize abutment surface area with the corresponding opposing teeth 354. Alternatively, teeth 354 may be involute as in the geometry of a gear tooth. It has been found that teeth having a total height, i.e., from the top flat contact surface to the bottom of the space between teeth, of 0.010 inches, a center to center distance between teeth of 0.032 inches and a center of tooth to center of the space between teeth distance of 0.016 inches is particularly suitable for gripping tissue effectively between opposing jaw members for most purposes. A radius of 0.0085 inches for the theoretical semicircle of the truncated semicircular teeth along with a height of 0.008 inches from the center of the theoretical circle having the same radius as the semicircle defining the teeth to the flat contact surface has been found particularly suitable. For such a jaw member, bulbous portion 356 having a radius of 0.018 inches for its rounded, distally extending shape has been found effective for preventing trauma to tissue both during manipulation of the instrument and during gripping procedures.

While the above embodiments have been described in the context of a Babcock clamp and tissue gripper jaw, other jaw structures may be advantageously formed in this fashion and in these configurations. Examples of other appropriate jaw structures include graspers, dissectors, forceps, etc.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic or laparoscopic surgical instrument comprising:

a handle assembly;

an endoscopic portion having a proximal end connected to said handle assembly and a distal end mounting a jaw mechanism, said jaw mechanism including a pair of jaw members disposed in opposing relation wherein at least one jaw member is movable such that said jaw members may be positioned in at least an open position and a closed position, each said jaw member having a distal portion defining a first plane and including an elongated tissue gripping face, and a proximal jaw mounting portion defining a second plane substantially perpendicular to said first plane, each said jaw member further including at least one arcuate transition area intermediate said proximal portion and said distal portion to facilitate jaw flexure.

2. An endoscopic or laparoscopic surgical instrument according to claim 1 wherein said opposing jaw members are relatively pivotal about a common point between said open position and said closed position.

3. An endoscopic or laparoscopic surgical instrument according to claim 1 wherein at least one of said tissue gripping faces includes a plurality of teeth disposed thereon such that when said jaw members are in said closed position tissue may be contacted by said teeth and gripped between said opposing jaw members.

4. An endoscopic or laparoscopic surgical instrument according to claim 3 wherein each of said teeth has a truncated semicircular geometry.

5. An endoscopic or laparoscopic surgical instrument according to claim 1 wherein each of said tissue gripping faces includes a plurality of teeth disposed thereon such that when said jaw members are in said closed position tissue may be gripped between said teeth of said opposing jaw members.

6. An endoscopic or laparoscopic surgical instrument according to claim 5 wherein each of said teeth has a truncated semicircular geometry.

7. An endoscopic or laparoscopic surgical instrument according to claim 5 wherein said teeth are disposed on each of said tissue gripping faces such that when said jaw members are in said closed position said teeth of each of said opposing jaw members abuts with corresponding teeth of said other opposing jaw member.

8. An endoscopic or laparoscopic surgical instrument according to claim 7 further comprising a linkage mechanism for pivoting said jaws between open and closed positions.

9. An endoscopic or laparoscopic surgical instrument according to claim 5, wherein said teeth are disposed on each of said tissue gripping faces such that when said jaw members are in said closed position said teeth of each of said opposing jaw members meshes with corresponding teeth of said other opposing jaw member.

10. An endoscopic or laparoscopic surgical instrument according to claim 1, further comprising an actuation mechanism extending from said handle assembly and adapted to remotely actuate said jaw mechanism.

11. An endoscopic or laparoscopic surgical instrument according to claim 1, wherein said elongated tissue gripping face of each of said jaw members is in close cooperative alignment with one another when said opposing jaw members are in said closed position.

12. An endoscopic or laparoscopic surgical instrument according to claim 1, wherein each of said distal portions of said jaw members has a semicircular face such that, when said jaw members are in said closed position, said semicircular face of said distal portions provides a substantially circular opening adapted for enclosing tissue therein.

13. An endoscopic or laparoscopic surgical instrument comprising:

a handle portion;

an endoscopic portion having a proximal end connected to said handle portion and a distal end mounting an atraumatic jaw mechanism, said atraumatic jaw mechanism including a pair of jaw members disposed in opposing relation wherein at least one jaw member is movable such that said jaw members may be positioned in at least an open position and a closed position, each said jaw member having a proximal portion including means for cooperating with a linkage member and a distal portion including a tissue gripping face disposed in a plane substantially perpendicular to the plane of said proximal portion, each said jaw member further including a plurality of arcuate transition areas intermediate said proximal portion and said distal portion.

14. An endoscopic or laparoscopic surgical instrument according to claim 13 wherein said distal portions of said jaw members each have a section of substantially semicircular shape such that, when said jaw members are in said closed position, said semicircular sections of said distal portions provide a substantially circular opening adapted for enclosing tissue therein.

15. An endoscopic or laparoscopic surgical instrument according to claim 23 wherein each of said tissue gripping faces includes a plurality of teeth disposed thereon such that when said jaw members are in said closed position tissue may be gripped between said teeth of said opposing jaw members.

16. An endoscopic or laparoscopic surgical instrument according to claim 13, further comprising an actuation mechanism extending from said handle portion and adapted to remotely actuate said jaw mechanism.

17. An endoscopic or laparoscopic surgical instrument comprising:

a handle assembly;

an endoscopic portion having a proximal end connected to said handle assembly and a distal end mounting an atraumatic jaw mechanism, said atraumatic jaw mechanism comprising:

a pair of individual jaw members disposed in opposing relation and pivotally connected to said endoscopic portion and movable between at least an open position and a closed position, said endoscopic portion having a fixed longitudinal orientation with respect to said pair of individual jaw members, each of said individual jaw members comprising:

a distal portion including a tissue engaging face;

a proximal portion including a pivot mechanism adapted to cooperate with a linkage mechanism; and a flexible intermediate portion interconnecting said distal portion and said proximal portion.

18. An endoscopic or laparoscopic surgical instrument according to claim 17, wherein said handle assembly includes a barrel portion, a stationary handle and a pivoting handle.

19. An endoscopic or laparoscopic surgical instrument according to claim 18, wherein said linkage mechanism comprises an inner rod member slidable within said endoscopic portion in response to movement of said handle assembly.

20. An endoscopic or laparoscopic surgical instrument according to claim 19, wherein said endoscopic portion comprises an outer tube member coaxially disposed about said inner rod.

21. An endoscopic or laparoscopic surgical instrument according to claim 20, further comprising a ratchet mechanism positioned within said barrel portion of said handle assembly, said ratchet mechanism engaging said body assembly to provide incremental positioning of said jaw members between said open and closed positions.

22. An endoscopic or laparoscopic surgical instrument according to claim 20, wherein said jaw members are precambered such that when they are pivoted to a closed position, a contact surface of the distal portions of said jaw members contact each other before said intermediate portions come in contact.

23. An endoscopic or laparoscopic surgical instrument according to claim 22, wherein said contact surface of the distal portions of said jaw members are provided with means for enhancing the grasping ability of said jaw members.

24. An endoscopic or laparoscopic surgical instrument according to claim 23, wherein said means for enhancing the grasping ability of said jaw members comprises a plurality of teeth formed on said contact surface.

25. An endoscopic or laparoscopic surgical instrument according to claim 23, wherein the distal portions of said jaw members are further provided with tissue expansion bores therein.

26. An endoscopic or laparoscopic surgical instrument according to claim 20, further comprising means for rotating said body assembly relative to said handle assembly to orient said jaw mechanism.

27. An endoscopic or laparoscopic surgical instrument according to claim 26, wherein said means for rotating said body assembly comprises a knob member circumferentially disposed about said body assembly and protruding radially outward from said body assembly through slots in said barrel portion in said handle assembly.

28. An endoscopic or laparoscopic surgical instrument according to claim 26, wherein said means for rotating said body assembly further comprises a stop means for arresting rotational movement of said body assembly.

29. An endoscopic or laparoscopic surgical instrument according to claim 17, wherein the distal portions of said jaw members each have a substantially semicircular shape such that, when said jaw members are pivoted to a closed position, the distal portions of said jaw members provide a substantially circular opening adapted for grasping tubular tissue.

30. An endoscopic or laparoscopic surgical instrument according to claim 17, wherein the distal portions of said jaw members are disposed in a plane substantially perpendicular to the plane of the proximal portions.

31. An endoscopic or laparoscopic surgical instrument according to claim 17, wherein the proximal portions of said jaw members are provided with camming slots for engaging a bearing surface on said linkage mechanism.

32. An endoscopic or laparoscopic surgical instrument according to claim 17, wherein the proximal portions of said jaw members include hinged connection means for connecting said jaw mechanism and said linkage mechanism.

33. An endoscopic or laparoscopic surgical instrument comprising:

- a handle assembly including a barrel portion, stationary handle and pivoting handle;
- a body assembly comprising a pair of coaxial members attached at one end to said handle assembly, including an inner rod member slidable within an outer tube member in response to movement of said handle assembly, said body assembly terminating at an end remote from said handle assembly in a reciprocally movable jaw mechanism, said jaw mechanism having a pair of individual jaw members disposed in opposing relation and pivotally connected to said outer tube member and movable between at least an open position and a closed position, each individual jaw member including a distal portion having a tissue engaging surface, a proximal portion including pivot means adapted to cooperate with said inner rod member and a flexible intermediate portion interconnecting said distal portion and said proximal portion, said body assembly further including a ratchet mechanism positioned within said barrel portion of said handle assembly, said ratchet mechanism including a rack means positioned on said inner rod member and a releasable pawl member which engages said ratchet means to provide for incremental positioning of said jaw members between said open and closed positions.

* * * * *